United States Patent
Stepanauskas et al.

(10) Patent No.: US 12,239,405 B2
(45) Date of Patent: Mar. 4, 2025

(54) ROBOTIC ASSISTED MOVEMENTS OF ELONGATED MEDICAL DEVICES

(71) Applicant: Corindus, Inc., Waltham, MA (US)

(72) Inventors: Jared Stepanauskas, Waltham, MA (US); Steven J. Blacker, Framingham, MA (US); Kaitlyn Drake, Boxborough, MA (US); Per Bergman, West Roxbury, MA (US); Sang-Joon Lee, Waban, MA (US); Nicholas Kottenstette, Sterling, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 1023 days.

(21) Appl. No.: 17/250,875

(22) PCT Filed: Sep. 18, 2019

(86) PCT No.: PCT/US2019/051800
§ 371 (c)(1),
(2) Date: Mar. 17, 2021

(87) PCT Pub. No.: WO2020/061240
PCT Pub. Date: Mar. 26, 2020

(65) Prior Publication Data
US 2022/0047344 A1 Feb. 17, 2022

Related U.S. Application Data

(60) Provisional application No. 62/803,899, filed on Feb. 11, 2019, provisional application No. 62/733,429, filed on Sep. 19, 2018.

(51) Int. Cl.
*A61B 5/00* (2006.01)
*A61B 34/37* (2016.01)
(Continued)

(52) U.S. Cl.
CPC ...... *A61B 34/37* (2016.02); *A61B 2034/2059* (2016.02); *A61B 2034/301* (2016.02);
(Continued)

(58) Field of Classification Search
CPC ............ A61B 34/37; A61B 2034/2059; A61B 2034/301; A61B 2034/742; A61B 34/25;
(Continued)

(56) References Cited

U.S. PATENT DOCUMENTS 5,116,350 A 5/1992 Stevens
5,314,407 A 5/1994 Auth et al.
(Continued)

FOREIGN PATENT DOCUMENTS

CN 1441654 9/2003
JP 2014131595 7/2014
(Continued)

OTHER PUBLICATIONS

International Search Report and Written Opinion for Corresponding International Application No. PCT/US2019/051800, mailed Jan. 14, 2020.
(Continued)

*Primary Examiner* — May A Abouelela

(57) ABSTRACT

An example system includes an apparatus having a first elongated medical device and a second elongated medical device; and a controller coupled to the apparatus. The controller is provided to determine a magnitude and a direction of linear translation of the first elongated medical device and responsive to the determined translation of the first elongated medical device, cause a linear translation of the second elongated medical device, the linear translation of the second elongated device having a substantially equal magnitude to the linear translation of the first elongated medical device and being in a direction opposite the direc-
(Continued)

tion of translation of the first elongated medical device. The controller is further provided to modify at least one parameter of the linear translation of either (a) the first elongated medical device or (b) the second elongated medical device in response to the determined translation of the first elongated device.

19 Claims, 18 Drawing Sheets

(51) Int. Cl.
- A61B 34/00 (2016.01)
- A61B 34/20 (2016.01)
- A61B 34/30 (2016.01)
- A61M 25/01 (2006.01)
- A61M 25/09 (2006.01)

(52) U.S. Cl.
CPC .... A61B 2034/742 (2016.02); A61M 25/0113 (2013.01); A61M 25/09041 (2013.01)

(58) Field of Classification Search
CPC .... A61B 90/37; A61B 34/30; A61M 25/0113; A61M 25/09041
See application file for complete search history.

(56) References Cited

U.S. PATENT DOCUMENTS

| | | | |
|---|---|---|---|
| 5,318,541 A | 6/1994 | Viera et al. | |
| 5,361,768 A | 11/1994 | Webler et al. | |
| 5,376,100 A | 12/1994 | Lefebvre | |
| 5,584,843 A | 12/1996 | Wulfman et al. | |
| 5,634,475 A * | 6/1997 | Wolvek | A61M 25/09041 600/585 |
| 5,779,722 A | 7/1998 | Shturman et al. | |
| 5,893,857 A | 4/1999 | Shturman et al. | |
| 6,129,734 A | 10/2000 | Shturman et al. | |
| 7,850,642 B2 | 12/2010 | Moll et al. | |
| 8,460,214 B2 | 6/2013 | Kuban et al. | |
| 8,676,301 B2 | 3/2014 | Coyle | |
| 9,050,438 B2 | 6/2015 | Rollins et al. | |
| 9,119,942 B1 | 9/2015 | Rollins et al. | |
| 9,314,306 B2 | 4/2016 | Yu | |
| 9,333,324 B2 | 5/2016 | Cohen et al. | |
| 9,408,669 B2 | 8/2016 | Kokish et al. | |
| 9,452,018 B2 | 9/2016 | Yu | |
| 9,566,414 B2 | 2/2017 | Wong et al. | |
| 9,731,096 B2 | 8/2017 | Bian et al. | |
| 9,907,614 B2 | 3/2018 | Grace et al. | |
| 9,956,382 B2 | 5/2018 | Hwang | |
| 9,962,229 B2 | 5/2018 | Blacker et al. | |
| 10,039,522 B2 | 8/2018 | Magnin et al. | |
| 10,052,458 B2 | 8/2018 | Fischer et al. | |
| 11,457,933 B2 * | 10/2022 | Akhlaghpour | A61B 34/20 |
| 2002/0177789 A1 | 11/2002 | Ferry et al. | |
| 2007/0179473 A1 | 8/2007 | Masters et al. | |
| 2008/0119846 A1 * | 5/2008 | Rioux | A61M 25/0194 606/41 |
| 2008/0140101 A1 | 6/2008 | Carley et al. | |
| 2008/0167663 A1 * | 7/2008 | De Mathelin | A61B 17/3403 901/41 |
| 2009/0326322 A1 * | 12/2009 | Diolaiti | A61B 34/30 600/112 |
| 2009/0326449 A1 | 12/2009 | Wang et al. | |
| 2010/0057099 A1 * | 3/2010 | Fujimoto | G09B 23/285 434/262 |
| 2010/0087811 A1 | 4/2010 | Herrin et al. | |
| 2010/0145259 A1 * | 6/2010 | Nash | A61B 17/32037 604/22 |
| 2010/0204613 A1 | 8/2010 | Rollins et al. | |
| 2010/0234873 A1 * | 9/2010 | Nagano | G01L 5/0038 254/133 R |
| 2011/0288560 A1 * | 11/2011 | Shohat | A61B 34/70 606/130 |
| 2012/0046600 A1 | 2/2012 | Kohler et al. | |
| 2012/0071822 A1 | 3/2012 | Romo et al. | |
| 2012/0101508 A1 | 4/2012 | Wook Choi et al. | |
| 2012/0172727 A1 | 7/2012 | Hastings et al. | |
| 2012/0232426 A1 | 9/2012 | Leiter | |
| 2013/0035537 A1 | 2/2013 | Wallace et al. | |
| 2013/0105552 A1 * | 5/2013 | Weir | A61B 34/37 227/176.1 |
| 2013/0190726 A1 * | 7/2013 | Kesner | A61M 25/0116 604/95.01 |
| 2013/0231631 A1 | 9/2013 | Murphy et al. | |
| 2014/0005718 A1 * | 1/2014 | Shelton, IV | A61B 34/30 606/205 |
| 2014/0243742 A1 | 8/2014 | Pacheco et al. | |
| 2014/0276233 A1 * | 9/2014 | Murphy | G01L 5/107 600/587 |
| 2014/0276389 A1 | 9/2014 | Walker | |
| 2014/0276938 A1 | 9/2014 | Hsu et al. | |
| 2014/0277333 A1 | 9/2014 | Lewis et al. | |
| 2014/0277334 A1 | 9/2014 | Yu et al. | |
| 2014/0309658 A1 | 10/2014 | Murphy et al. | |
| 2014/0316448 A1 | 10/2014 | Higgins | |
| 2015/0148816 A1 | 5/2015 | Govari et al. | |
| 2016/0067448 A1 | 3/2016 | Blacker et al. | |
| 2016/0101267 A1 | 4/2016 | Kelly | |
| 2016/0184552 A1 | 6/2016 | Hou et al. | |
| 2016/0228249 A1 * | 8/2016 | Mantanus | A61F 2/2436 |
| 2016/0228684 A1 | 8/2016 | Martin | |
| 2016/0354582 A1 | 12/2016 | Yu et al. | |
| 2017/0043137 A1 | 2/2017 | Felkins et al. | |
| 2017/0086928 A1 * | 3/2017 | Auld | A61B 90/50 |
| 2017/0128697 A1 * | 5/2017 | Moisa | A61N 1/362 |
| 2017/0151421 A1 | 6/2017 | Asher | |
| 2017/0252058 A1 | 9/2017 | Bar-Cohen et al. | |
| 2017/0259048 A1 | 9/2017 | Matlock et al. | |
| 2017/0312481 A1 * | 11/2017 | Covington | H02K 11/24 |
| 2017/0368318 A2 | 12/2017 | Asher | |
| 2018/0056044 A1 * | 3/2018 | Choi | A61B 34/30 |
| 2018/0110968 A1 | 4/2018 | Ngo-Cho et al. | |
| 2018/0177515 A1 | 6/2018 | Boyle et al. | |
| 2018/0311473 A1 | 11/2018 | Laby et al. | |
| 2019/0059985 A1 * | 2/2019 | Shelton, IV | A61B 17/07207 |
| 2019/0059986 A1 * | 2/2019 | Shelton, IV | A61B 18/1447 |
| 2019/0076208 A1 * | 3/2019 | Prentakis | A61M 25/0116 |
| 2019/0175887 A1 * | 6/2019 | Shameli | A61M 25/0113 |
| 2019/0192822 A1 * | 6/2019 | Kim | A61L 29/041 |
| 2019/0239890 A1 * | 8/2019 | Stokes | A61B 34/37 |
| 2020/0022653 A1 * | 1/2020 | Moisa | A61N 1/36514 |
| 2020/0022764 A1 * | 1/2020 | Flexman | G02B 6/022 |
| 2020/0069379 A1 * | 3/2020 | Betsugi | A61B 34/25 |
| 2020/0129239 A1 * | 4/2020 | Bianchi | G06T 19/006 |
| 2020/0275942 A1 * | 9/2020 | Iordachita | A61F 9/007 |
| 2020/0281673 A1 * | 9/2020 | Suzuki | A61B 17/29 |
| 2024/0238617 A1 * | 7/2024 | Roberts | A61B 34/35 |

FOREIGN PATENT DOCUMENTS

| | | |
|---|---|---|
| JP | 2016000221 | 1/2016 |
| WO | 2016090270 | 6/2016 |

OTHER PUBLICATIONS

Feng, Zhen-Qiu, et al. "Design and evaluation of a bio-inspired robotic hand for percutaneous coronary intervention." 2015 IEEE International Conference on Robotics and Automation (ICRA). 2015.

Ji, Cheng, Zeng-Guang Hou, and Xiao-Liang Xie. "Guidewire navigation and delivery system for robot-assisted cardiology interventions." IEEE 10th International Conference on Cognitive Informatics and Cognitive Computing (ICCI-CC'11). IEEE, 2011.

Wang, Jun-qiang, et al. "Computer-assisted navigation systems for insertion of cannulated screws in femoral neck fractures: a comparison of bi-planar robot navigation with optoelectronic navigation

(56) References Cited

OTHER PUBLICATIONS in a Synbone hip model trial." Chinese medical journal 124.23 (2011): 3906-3911.

* cited by examiner

```
function y = fcn(e_GW_t,e_BSC_t)
e_max=5; %Don't allow GC to move if either devices tracking error is greater than 5 mm.
e_inf = max(abs([e_GW_t,e_BSC_t])); %e_inf is the max of the absolute of all proximal devices being fixed.
k_reduce = 1 - e_inf/(e_max); %reduce the velocity command by 1 - e_inf divided by e_max
y = max(0,k_reduce); %ensure that the velocity command is zero if e_inf > e_max
```

ROBOTIC ASSISTED MOVEMENTS OF ELONGATED MEDICAL DEVICES

CROSS-REFERENCE TO RELATED APPLICATIONS

This application claims priority to and benefit of U.S. Provisional Application Ser. No. 62/733,429, titled "ROBOTIC ASSISTED MOVEMENTS OF PERCUTANEOUS DEVICES," filed on Sep. 19, 2018, and U.S. Provisional Application Ser. No. 62/803,899, titled "PROXIMAL DEVICE FIXATION WITH SINGLE FAULT", filed on Feb. 11, 2019, each of which is hereby incorporated by reference in its entirety and for all purposes.

FIELD

The present invention relates generally to the field of catheter procedure systems and, in particular, a robotic system and method for automated movement of an elongated medical device such as a guidewire and/or catheter.

BACKGROUND

Catheters (and other elongated medical devices) may be used for many minimally-invasive medical procedures for the diagnosis and treatment of diseases of various vascular systems, including neurovascular interventional (NVI) also known as neurointerventional surgery, percutaneous coronary intervention (PCI) and peripheral vascular intervention (PVI). These procedures typically involve navigating a guidewire through the vasculature, and via the guidewire advancing a working catheter to deliver therapy. The catheterization procedure starts by gaining access into the appropriate vessel, such as an artery or vein, with a sheath or guide catheter using standard percutaneous techniques. The sheath or guide catheter is then advanced over a diagnostic guidewire to the primary location such as an internal carotid artery for NVI, a coronary ostium for PCI or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., fluoroscope) to obtain a cine with a contrast injection and select a fixed frame for use as a roadmap to navigate the guidewire or catheter to the target location, for example a lesion. Contrast-enhanced images are also obtained while the physician delivers the guidewire or catheter device so that the physician can verify that the device is moving along the correct path to the target location. While observing the anatomy using fluoroscopy, the physician manipulates the proximal end of the guidewire or catheter to direct the distal tip into the appropriate vessels toward the lesion and avoid advancing into side branches.

Robotic catheter procedure systems have been developed that may be used to aid a physician in performing catheterization procedures such as, for example, NVI, PCI and PVI. Examples of neurovascular intervention (NVI) catheter procedures include coil embolization of aneurysms, liquid embolization of arteriovenous malformations and mechanical thrombectomy of large vessel occlusions in the setting of acute ischemic stroke. In NVI, the physician uses a robotic system to gain lesion access by manipulating a neurovascular guidewire and microcatheter to deliver the therapy to restore normal blood flow. The access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several coils are deployed into the aneurysm through the microcatheter and used to embolize the aneurysm. For treating arteriovenous malformations, a liquid embolic is injected into the malformation via a microcatheter. Mechanical thrombectomy to treat vessel occlusions can be achieved either through aspiration or use of a stent retriever. Aspiration is either done directly through the microcatheter, or with a larger bore aspiration catheter. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or FFR measurements.

In PVI, the physician uses a robotic system to deliver the therapy and restore blood flow with techniques similar to NVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

SUMMARY

In accordance with an embodiment, a system comprises an apparatus having a first elongated medical device and a second elongated medical device and a controller coupled to the apparatus. The controller is provided to determine a magnitude and a direction of linear translation of the first elongated medical device, and responsive to the determined translation of the first elongated medical device, cause a linear translation of the second elongated medical device, the linear translation of the second elongated device having a substantially equal magnitude to the linear translation of the first elongated medical device and being in a direction opposite the direction of translation of the first elongated medical device. The controller is further provided to modify at least one parameter of the linear translation of either (a) the first elongated medical device or (b) the second elongated medical device.

In an example, modifying the at least one parameter includes limiting the magnitude of the translation of the second elongated medical device. The controller may modify the at least one parameter in response to a determination of a loss of traction for linear translation of the second elongated medical device.

In one example, the at least one parameter includes the magnitude or speed of the translation of the first elongated medical device. In one example, the first elongated medical device is a catheter and the second elongated medical device is a guidewire.

In one example, the linear motion of the first elongated medical device and the linear motion of the second elongated medical device are substantially simultaneous.

In one example, the controller identifies an unintended movement of the second elongated medical device, and wherein the controller suspends modification of the at least one parameter of the first elongated medical device or the second elongated medical device upon identification of the unintended movement of the second elongated medical device.

In one example, the controller detects the absence or presence of the second elongated medical device based on detection of movement of the second elongated medical device via an input from a sensor. The controller may suspend modification of the at least one parameter of the first elongated medical device or the second elongated medical device when the controller detects the absence of the second elongated medical device.

In one example, the controller terminates the linear translation of the second elongated medical device when a linear translation of the second elongated medical device is within a first threshold of the determined translation of the first elongated medical device. The controller may resume the linear translation of the second elongated medical device when a linear translation of the second elongated medical device is greater than a second threshold of the determined translation of the first elongated medical device, wherein the second threshold is greater than the first threshold.

In one example, the system further includes one or more additional elongated medical devices the behavior of which are constrained in the same manner as second elongated medical device.

In accordance with an embodiment, a system comprises an elongated medical device apparatus having at least one elongated medical device and a control station coupled to the elongated medical device apparatus. The control station includes a control module to, in response to a user command, implement a predetermined movement pattern of a proximal portion of the elongated medical device. The predetermined movement pattern is oscillation of the elongated medical device about a longitudinal axis of the elongated medical device. An auxiliary command modifies the amplitude of the oscillation.

In one example, the auxiliary command modifies the amplitude of the oscillation by reducing or increasing the amplitude.

In one example, the auxiliary command modifies the amplitude of the oscillation by skewing the amplitude. The skewing may include moving a center position of the oscillation.

In one example, the auxiliary command is received from either the control module or from an operator input device.

In one example, the oscillation of the elongated medical device has a first amplitude when advancing through a vessel and a second amplitude when crossing an obstacle.

In one example, the predetermined movement pattern is activated only upon linear movement of the elongated medical device. The control module may suspend the oscillation of the elongated medical device when the linear movement is stopped or reversed or jogged.

In one example, at least one parameter of the oscillation is configurable, the parameter being a frequency, amplitude or rotational speed.

In accordance with an embodiment, a system comprises an elongated medical device apparatus having at least one elongated medical device and a control station. The control station includes a control module to, in response to a user command for linear translation of the elongated medical device, implement a movement pattern of a proximal portion of the elongated medical device. The movement pattern is the linear translation accompanied with continuous unidirectional rotation of the elongated medical device about a longitudinal axis of the elongated medical device. The movement pattern is activated during forward linear translation and suspended during reverse linear translation.

In one example, an auxiliary command can modify the rate of rotation of the movement pattern.

In accordance with an embodiment, a system comprises an elongated medical device apparatus having at least one elongated medical device and a control station. The control station includes a control module to, in response to a user command, implement a predetermined movement pattern of a proximal portion of the elongated medical device. The predetermined movement pattern is linear oscillation of the elongated medical device, the linear oscillation including alternating forward and reverse linear movement of the elongated medical device. The movement pattern is activated during forward linear translation and suspended during reverse linear translation.

In accordance with an embodiment, a system comprises an apparatus having a first elongated medical device and a second elongated medical device and a controller coupled to the apparatus. The controller is provided to receive a command for a movement of the first elongated medical device, actuate the first elongated medical device, detect the movement of the first elongated medical device, and responsive to the detected linear translation of the elongated medical device, synchronize movement of the second elongated medical device to the movement of the first elongated medical device.

In one example, the movement of the first elongated medical device and the synchronized movement of the second elongated medical device includes small alternatingly forward and backward linear movement with a resultant forward linear translation.

BRIEF DESCRIPTION OF THE DRAWINGS

The invention will become more fully understood from the following detailed description, taken in conjunction with the accompanying drawings, wherein the reference numerals refer to like parts in which.

DETAILED DESCRIPTION

Figure 1:
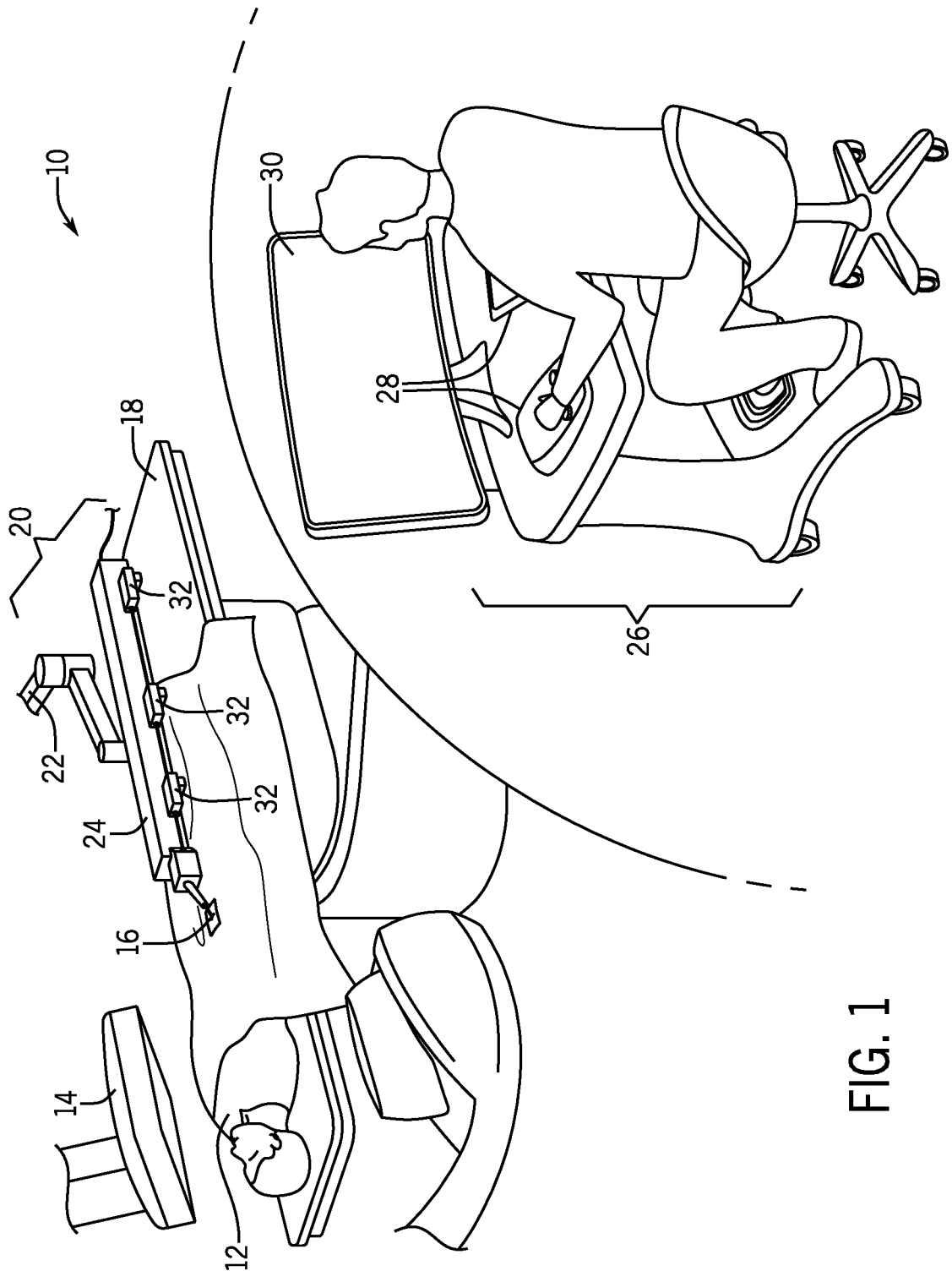
FIG. 1 is a perspective view of an exemplary catheter-based procedure system in accordance with an embodiment.

FIG. 1 is a perspective view of an exemplary catheter-based procedure system in accordance with an embodiment. In FIG. 1, a catheter-based procedure system 10 may be used to perform catheter-based medical procedures, e.g., percutaneous intervention procedure such as, a percutaneous coronary intervention (PCI), e.g., STEMI, a neurovascular interventional procedure (NVI) (e.g., to treat an emergent large vessel occlusion (ELVO)), peripheral vascular intervention procedures (PVI), e.g., for critical limb ischemia (CLI), etc. Catheter-based medical procedures may include diagnostic catheterization procedures during which one or more catheters (or other elongated medical devices (EMDs)) are used to aid in the diagnosis of a patient's disease. For example, during one embodiment of a catheter-based diagnostic procedure, a contrast media is injected onto one or more arteries through a catheter and an image of the patient's vasculature is taken. Catheter-based medical procedures may also include catheter-based therapeutic procedures (e.g., angioplasty, stent placement, treatment of peripheral vascular disease, clot removal, arterial venous malformation therapy, treatment of aneurysm, etc.) during which a catheter (or other elongated medical device) is used to treat a disease. Therapeutic procedures may be enhanced by the inclusion of adjunct devices 54 (shown in FIG. 2) such as, for example, intravascular ultrasound (IVUS), optical coherence tomography (OCT), fractional flow reserve (FFR), etc. It should be noted, however, that one skilled in the art would recognize that certain specific percutaneous intervention devices or components (e.g., type of guidewire, type of catheter, etc.) will be selected based on the type of procedure that is to be performed. Catheter-based procedure system 10 is capable of performing any number of catheter-based medical procedures with minor adjustments to accommodate the specific percutaneous intervention devices to be used in the procedure.

Figure 2:
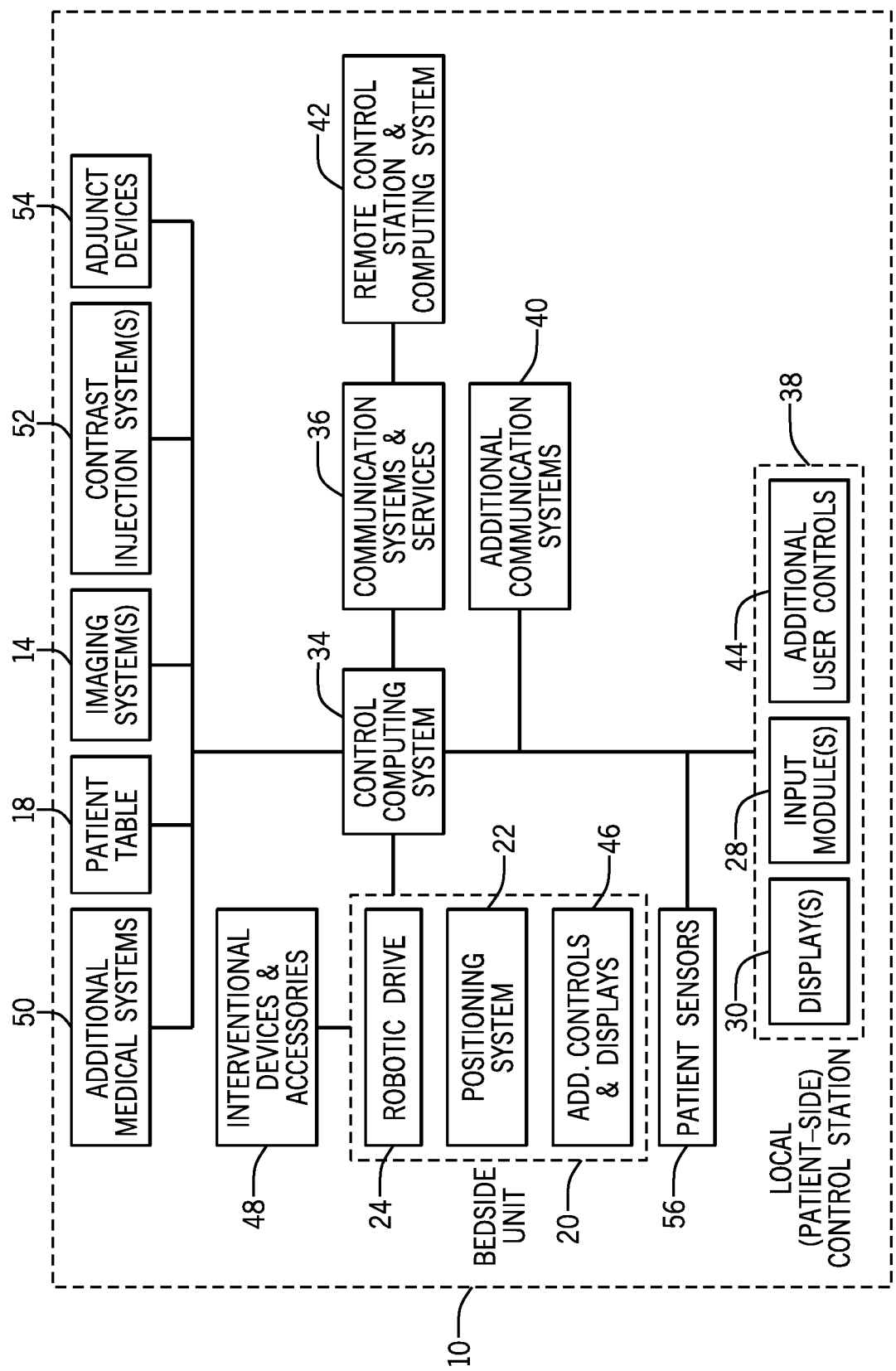
FIG. 2 is a schematic block diagram of an exemplary catheter-based procedure system in accordance with an embodiment.

Catheter-based procedure system 10 includes, among other elements, a bedside unit 20 and a control station 26. An overall view of the main building blocks of catheter-based procedure system 10 is shown in FIG. 2, discussed further below. Bedside unit 20 incudes a robotic drive 24 and a positioning system 22 (e.g., a robotic arm, an articulated arm, a holder, etc.) that are located adjacent to a patient. Bedside unit 20 may also include controls and displays 46 (shown in FIG. 2). For example, controls and displays may be located on a housing of the robotic drive 24. Patient 12 is supported on a table 18. Generally, the robotic drive 24 may be equipped with the appropriate percutaneous intervention devices or other accessories 48 (shown in FIG. 2) (e.g., guidewires, various types of catheters, balloon catheters, stent delivery systems, stent retrievers, embolization coils, liquid embolics, aspiration pumps, contrast media, medicine, etc.) to allow the user to perform a catheter-based medical procedure via a robotic system by operating various controls such as the controls located at the control station 26. Bedside unit 20, and in particular robotic drive 24, may include any number and/or combination of components to provide bedside unit 20 with the functionality described herein. The robotic drive 24 includes a plurality of device modules 32 mounted to a rail 60 (shown in FIG. 3). Each of the device modules 32 may be used to drive an elongated medical device such as a catheter or guidewire. For example, the robotic drive 24 may be used to automatically feed a guidewire into a diagnostic catheter and into a guide catheter seated in an artery of the patient 12. One or more devices, e.g., an EMD, enter the body of the patient (e.g., a vessel) at an insertion point 16 using, for example, an introducer and introducer sheath.

Bedside unit 20 is in communication with control station 26, allowing signals generated by the user inputs of control station 26 to be transmitted to bedside unit 20 to control the various functions of bedside unit 20. As discussed further below with respect to FIG. 2, the control station 26 may include a control computing system 34 (shown in FIG. 2) or be coupled to the bedside unit 20 through a control computing system 34. Bedside unit 20 may also provide feedback signals (e.g., loads, speeds, operating conditions, warning signals, error codes, etc.) to control station 26, control computing system 34 (shown in FIG. 2), or both. Communication between the control computing system and various components of the catheter-based procedure system 10 may be provided via a communication link that may be a wireless connection, cable connections, or any other means capable of allowing communication to occur between components. Control station 26 or other similar control system may be located either at a local site (e.g., local control station 38 shown in FIG. 2) or at a remote site (e.g., remote control station and computer system 42 shown in FIG. 2). The catheter procedure system 10 may be operated by a control station at the local site, a control station at a remote site, or both the local control station and the remote control station at the same time. At a local site, an operator and control station 26 are located in the same room or an adjacent room to the patient 12 and bedside unit 20. As used herein, a local site is the location of the bedside system 20 and a patient 12 or subject and the remote site is the location of an operator (e.g., a doctor) and a control station 26 used to control the bedside system 20 remotely. A control station 26 (and a control computing system) at a remote site and the bedside unit 20 and/or a control computing system at a local site may be in communication using communication systems and services 36 (shown in FIG. 2), for example, through the Internet. In an embodiment, the remote site and the local (patient) site are away from one another, for example, different rooms in the same building, different buildings in the same city, different cities, or other different locations where the remote site does not have physical access to the bedside unit 20 or patient 12 at the local site.

Control station 26 generally includes one or more input modules 28 configured to receive user inputs to operate various components or systems of catheter-based procedure system 10. In the embodiment shown, control station 26 allows the user to control bedside unit 20 to perform a catheter-based medical procedure. For example, input modules 28 may be configured to cause bedside unit 20 to perform various tasks using various percutaneous intervention devices (e.g., elongated medical devices) interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., axial and rotational movement) of the components of the bedside unit 20 including the percutaneous intervention devices.

In one embodiment, input modules 28 may include a touch screen, one or more joysticks, scroll wheels, and/or buttons. In addition to input modules 28, the control station 26 may use additional user controls 44 (shown in FIG. 2) such as foot switches and microphones for voice commands, etc. Input modules 28 may be configured to advance, retract, or rotate various components and percutaneous intervention devices such as, for example, a guidewire, and one or more catheters or microcatheters. Buttons may include, for example, an emergency stop button, a multiplier button, device selection buttons and automated move buttons. When an emergency stop button is pushed a relay is triggered to cut the power supply to bedside unit 20. When in a speed control mode, a multiplier button acts to increase or decrease the speed at which the associated component is moved in response to a manipulation of input modules 28. When in a position control mode, a multiplier button changes the mapping between input distance and the output commanded distance. Device selection buttons allow the user to select which of the percutaneous intervention devices loaded into the robotic drive 24 are controlled by input modules 28. Automated move buttons are used to enable algorithmic movements that the catheter-based procedure system 10 will perform on a percutaneous intervention device without direct command from the user. In one embodiment, input modules 28 may include one or more controls or icons (not shown) displayed on touch screen, that, when activated, causes operation of a component of the catheter-based procedure system 10. Input modules 28 may also include a balloon or stent control that is configured to inflate or deflate a balloon and/or deploy a stent. Each of the modules may include one or more buttons, scroll wheels, joysticks, touch screen, etc. that may be desirable to control the particular component to which the control is dedicated. In addition, a touch screen may display one or more icons (not shown) related to various portions of input modules 28 or to various components of catheter-based procedure system 10.

Control station 26 may include a display 30. In other embodiments, the control station 26 may include two or more displays 30. Display 30 may be configured to display information or patient specific data to the user located at control station 26. For example, display 30 may be configured to display image data (e.g., x-ray images, MRI images, CT images, ultrasound images, etc.), hemodynamic data (e.g., blood pressure, heart rate, etc.), patient record information (e.g., medical history, age, weight, etc.), lesion or treatment assessment data (e.g., IVUS, OCT, FFR, etc.). In addition, display 30 may be configured to display procedure specific information (e.g., procedural checklist, recommendations, duration of procedure, catheter or guidewire position, volume of medicine or contrast agent delivered, etc.). Further, display 30 may be configured to display information to provide the functionalities associated with control computing system 34 (shown in FIG. 2). Display 30 may include touch screen capabilities to provide some of the user input capabilities of the system.

Catheter-based procedure system 10 also includes an imaging system 14. Imaging system 14 may be any medical imaging system that may be used in conjunction with a catheter based medical procedure (e.g., non-digital x-ray, digital x-ray, CT, MRI, ultrasound, etc.). In an exemplary embodiment, imaging system 14 is a digital x-ray imaging device that is in communication with control station 26. In one embodiment, imaging system 14 may include a C-arm (as shown in FIG. 1) that allows imaging system 14 to partially or completely rotate around patient 12 in order to obtain images at different angular positions relative to patient 12 (e.g., sagittal views, caudal views, anterior-posterior views, etc.).

Imaging system 14 may be configured to take x-ray images of the appropriate area of patient 12 during a particular procedure. For example, imaging system 14 may be configured to take one or more x-ray images of the head to diagnose a neurovascular condition. Imaging system 14 may also be configured to take one or more x-ray images during a catheter-based medical procedure (e.g., real time images) to assist the user of control station 26 to properly position a guidewire, guide catheter, microcatheter, stent retriever, coil, stent, balloon, etc. during the procedure. The image or images may be displayed on display 30. In particular, images may be displayed on display 30 to allow the user to, for example, accurately move a guide catheter or guidewire into the proper position.

Referring to FIG. 2, a block diagram of catheter-based procedure system 10 is shown according to an exemplary embodiment. Catheter-procedure system 10 may include a control computing system 34. Control computing system 34 may physically be, for example, part of control station 26 (shown in FIG. 1). Control computing system 34 may generally be an electronic control unit suitable to provide catheter-based procedure system 10 with the various functionalities described herein. For example, control computing system 34 may be an embedded system, a dedicated circuit, a general-purpose system programed with the functionality described herein, etc. Control computing system 34 is in communication with bedside unit 20, communications systems and services 36 (e.g., Internet, firewalls, cloud services, session mangers, a hospital network, etc.), a local control station 38, additional communications systems 40 (e.g., a telepresence system), a remote control station and computing system 42, and patient sensors 54 (e.g., electrocardiogram ("ECG") devices, electroencephalogram ("EEG") devices, blood pressure monitors, temperature monitors, heart rate monitors, respiratory monitors, etc.). The control computing system is also in communication with imaging system 14, patient table 18, additional medical systems 50, contrast injection system 52 and adjunct devices 54 (e.g., IVUS, OCT, FFR, etc.). The bedside unit 20 includes a robotic drive 24, a positioning system 22 (e.g., a robotic arm, articulated arm, holder, etc.) and may include additional controls and displays 46. As mentioned above, the additional controls and displays may be located on a housing of the robotic drive 24. Interventional devices and accessories 48 (e.g., guidewires, catheters, etc.) interface to the bedside unit 20. In an embodiment, interventional devices and accessories 48 may include specialized devices (e.g., IVUS catheter, OCT catheter, FFFR wire, diagnostic catheter for contrast, etc.) which interface to their respective adjunct devices 54, namely, an IVUS system, an OCT system, an FFR system, etc.

In various embodiments, control computing system 34 is configured to generate control signals based on the user's interaction with input modules 28 (e.g., of a control station 26 (shown in FIG. 1) such as a local control station 38 or a remote control station 42) and/or based upon information accessible to control computing system 34 such that a medical procedure may be performed using catheter-based procedure system 10. The local control station 38 includes one or more displays 30, one or more input modules 28 and additional user controls 44. The remote control station and computing system 42 may include similar components to the local control station 38. The remote 42 and local 38 control stations can be different and tailored based on their required functionalities. The additional user controls 44 may include one or more foot input devices. The foot input device may be configured to allow the user to select functions of the imaging system 14 such as turning on and off the x-ray and scrolling through different stored images. In another embodiment, a foot input device may be configured to allow the user to select which devices are mapped to scroll wheels included in input modules 28. Additional communication systems 40 (e.g., audio conference, video conference, telepresence, etc.) may be employed to help the operator interact with the patient, angio-suite staff or equipment in the vicinity of the bedside.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, systems to restrict access or use of catheter-based procedure system 10, etc.

Figure 3:
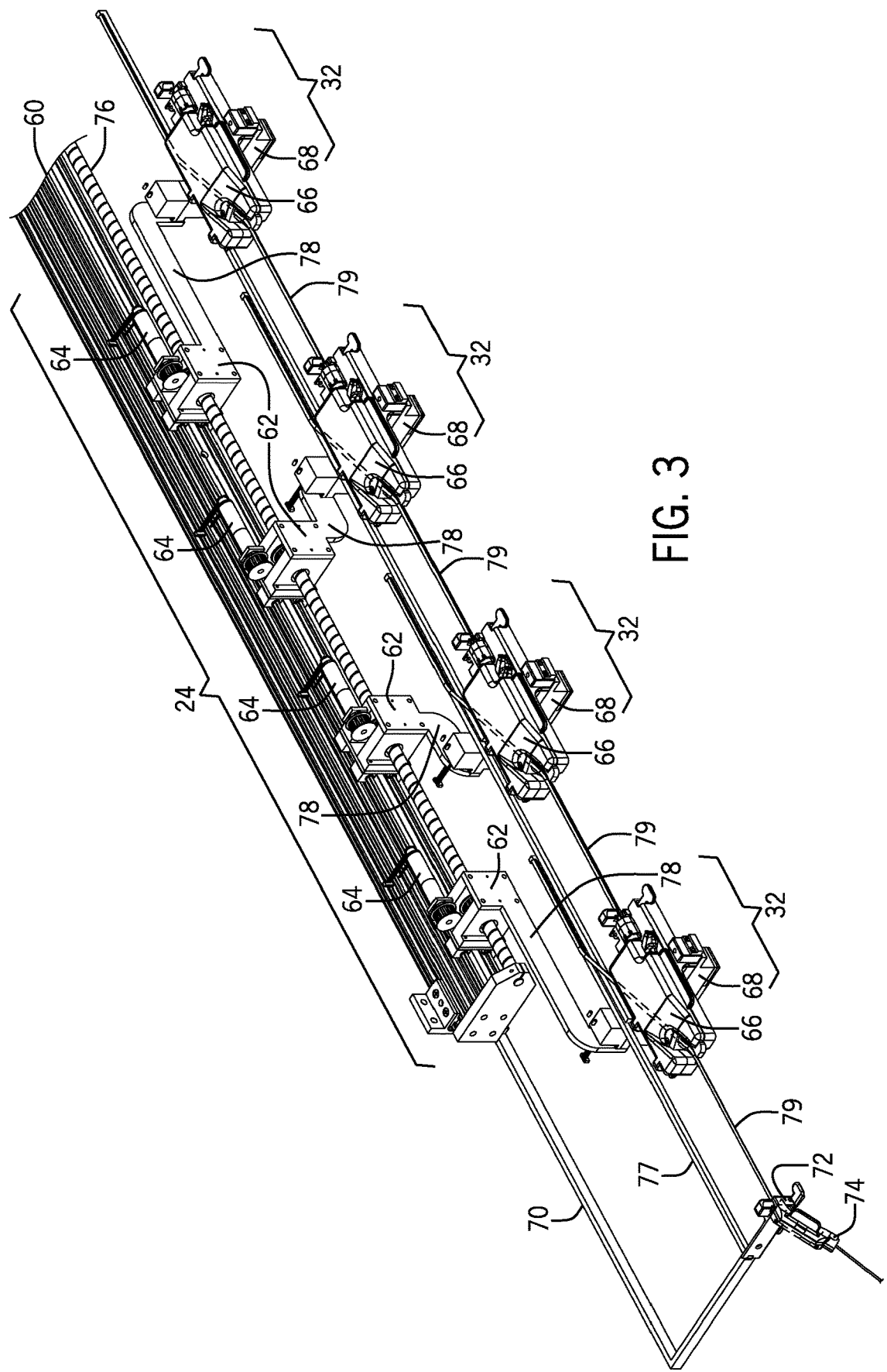
FIG. 3 is a perspective view of a robotic drive for a catheter-based procedure system in accordance with an embodiment.

As mentioned, control computing system 34 is in communication with bedside unit 20 which includes a robotic drive 24, a positioning system 22 and may include additional controls and displays 44, and may provide control signals to the bedside unit to control the operation of the motors and drive mechanisms used to drive the percutaneous intervention devices (e.g., guidewire, catheter, etc.). The various drive mechanisms may be provided as part of a robotic drive 24 (shown in FIGS. 1 and 2). FIG. 3 is a perspective view of a robotic drive for a catheter procedure system in accordance with an embodiment. In FIG. 3, a robotic drive 24 includes multiple device modules 32 coupled to a linear rail 60. Each device module 32 is coupled to the rail 60 via a stage 62 slidably mounted to the rail 60. A device module 32 may be connected to a stage 62 using a connector such as an offset bracket 78. In another embodiment, the device module 32 is directly mounted to the stage 62. Each stage 62 may be independently actuated to move linearly along the rail 60. Accordingly, each stage 62 (and the corresponding device module 32 coupled to the stage 62) has independent motion relative to each other and the rail 60. A drive mechanism is used to actuate each stage 62. In the embodiment shown in FIG. 3, the drive mechanism includes independent stage translation motors 64 coupled to each stage 62 and a stage drive mechanism 76, for example, a lead screw. In FIG. 2, the stages 62 and drive modules 32 are in a serial drive configuration.

Each device module 32 includes a drive module 68 and a cassette 66 mounted on and coupled to the drive module 68. In FIG. 3, each cassette 66 is shown mounted to the drive module 68 in a vertical orientation. In other embodiments, the cassette 66 may be mounted to the drive module 68 in other mounting orientations. The cassette 66 is sterile and is configured to house and support an elongated medical device (not shown). In addition, the cassette 66 may include mechanisms to provide at least one additional degree of freedom, for example, rotation, to the elongated medical device when the cassette is coupled to the drive module 68. The drive module 68 includes at least one coupler to provide a power interface to the mechanisms in the cassette 66 to provide the additional degree of freedom. Each cassette 66 also houses a device support 79 that prevents elongated medical devices from buckling. The robotic drive 24 may also include a device support connection 72 connected to a device support 79, a distal-define arm 70 and a support arm 77. In addition, an introducer interface support (redirector) 74 may be connected to the device support connection 72 and an elongated medical device (e.g., an introducer sheath). The configuration of robotic drive 24 has the benefit of reducing volume and weight of the drive robotic drive 24 by merging actuators onto a single rail.

Catheter-based medical procedures may include diagnostic catheterization procedures performed in the heart, brain or peripheral vasculature, during which one or more catheters are used to aid in the diagnosis of a patient's disease. For example, in one example, a contrast media is injected onto one or more coronary arteries through a catheter and an image of the patient's heart is taken. Catheter-based medical procedures may also include catheter-based therapeutic procedures performed in the heart, brain or peripheral vasculature (e.g., angioplasty, stent placement, treatment of peripheral vascular disease, clot removal, arterial venous malformation therapy, treatment of aneurysm, etc.) during which a catheter is used to treat a disease. It should be noted that one skilled in the art would recognize that certain specific percutaneous intervention devices or components (e.g., type of guidewire, type of catheter, etc.) will be selected based on the type of procedure that is to be performed.

As used herein, the direction distal is the direction toward the patient and the direction proximal is the direction away from the patient. For example, the distal end of an elongate medical device (EMD), such as a guide catheter, refers to the end that is inserted into the patient, while the proximal end of the EMD refers to the end coupled to the bedside unit 20 described above. The term up and upper refers to the general direction away from the direction of gravity and the term bottom, lower and down refers to the general direction of gravity. The term front refers to the side of the robotic mechanism that faces a user and away from the articulating arm. The term rear refers to the side of the robotic mechanism that is closest to the articulating arm. The term inwardly refers to the inner portion of a feature. The term outwardly refers to the outward portion of a feature.

To perform a procedure, the elongated medical devices, such as a guide catheter, guidewire and/or working catheter are inserted into the patient. In one example type of intervention procedure, a guide catheter is inserted into a patient's femoral artery through an introducer and positioned proximate the coronary ostium of a patient's heart.

The guide catheter maintains a linear position along its longitudinal axis within drive module 32. During a medical procedure such as percutaneous coronary intervention (PCI), a guide catheter is used to guide other elongated medical devices, such as a guidewire and balloon stent catheter, into a patient to conduct, for example, an exploratory diagnosis or to treat a stenosis within a patient's vascular system. The distal end of the guide catheter may be seated within the ostium of the patient's heart. The robotic drive 24 drives a guidewire and/or a working catheter such as a balloon stent catheter in and out of a patient. The guidewire and working catheter are driven within the guide catheter between the distal end of the robotic mechanism 212 and the patient.

Linear movement of a percutaneous device also referred to herein as an elongated medical device (EMD) is movement along the longitudinal axis of the EMD. The longitudinal axis of the EMD is defined as the path extending from a proximal end of the EMD to the distal end of the EMD. If the EMD is rigid than the entire EMD is positioned such that the proximal end of the EMD, the distal end of the EMD and all of the EMD therebetween is on a straight line. In this case the longitudinal axis of the EMD would be defined by the straight line. However, if the EMD is flexible and moves through a path either in the robotic drive mechanism or through a non-linear vasculature path then a certain portion of the EMD will not be along a straight line defined by the proximal end of the EMD and the distal end of the EMD. However, a center portion of the EMD that is moving through the non-linear portion of the robotic drive or the vasculature would still be on the longitudinal axis of the EMD. Linear motion is then movement of the EMD along the longitudinal axis of the EMD. Movement of the EMD in a direction away from the proximal end into a patient is forward or fore linear motion and movement of the EMD away from the distal end or out of the patient is reverse or aft linear motion.

Rotational Movement of the EMD is defined as rotation of the EMD about the longitudinal axis. Clockwise rotational movement of the EMD is the clockwise rotation of the EMD about the longitudinal axis of the EMD at the point at which the drive mechanism In one example, a first user controller or user input provides instructions to move an EMD. In one embodiment the first or primary user controller is a joystick to provide multiple degree of movement instructions. In one embodiment moveable about a pivot in a forward and reverse direction from a center neutral position provides instructions to move the EMD in a forward or reverse position respectively. In one embodiment a linear deadband is defined as the position of the joystick in which no forward or reverse command is provided. In one example movement of the joystick 3 degrees forward or reverse will not in any movement of the EMD. In one embodiment rotation of the joy stick about a longitudinal axis provides a rotational instruction to the EMD. Such that clockwise rotation of the joystick results in clockwise rotation of the EMD and counterclockwise rotation of the joystick results in counterclockwise rotation of the EMD. However, instruction to provide rotation of the EMD only occurs once the joystick is rotated beyond a rotational deadband which in one embodiment is 3 degrees in either direction. It is contemplated that the rotational deadband may be less than 3 degrees. In one embodiment the rotational deadband is 2 degrees and in one embodiment the rotational deadband is more than 3 degrees.

An operator utilizes robotic system as described herein to drive an EMD for a number of different vasculature procedures. The vasculature procedures include lesion crossing, vessel navigation, lesion measurements, lesion assessment, lesion preparation, self-expanding stent deployment, and device stabilization during guide catheter manipulation, among others.

The various user input devices allow an operator to control the movement of one, multiple or all EMDs of the system 10. For example, the operator may control movement of the guide catheter, microcatheter, guidewire or other EMDs, individually or together. To facilitate effectiveness of a procedure using an example catheter-based procedure system, various examples described herein allow the operator to select one or more modes of robotic movement for assistance during a procedure. Such modes of robotic movement can cause the robotic drive to implement movement pattern including certain repetitive movements with or without additional operator input. As used herein, "pattern" refers to a sequence, such as a sequence of movements or commands, for example. A movement may be enabled, in some examples, with certain default values which may be changed with further operator input. Various movements are described below with reference to FIGS. 4-9. Certain movements may be applied to any or all of the EMDs used for a particular procedure, while other movements may be useful for only certain types of EMDs.

In the figures described below, various movement patterns are illustrated at the distal end of the EMD(s), or the end of the EMD that is inserted into the patient. In various examples, the desired movement pattern is implemented at the proximal portion of the EMD through actuators (e.g., drive motor or drive tires). In other words, the drive motor may be actuated to cause the desired movement at the proximal portion of the EMD to transmit movement to the distal end of the EMD. The precise movement at the distal end may or may not match the movement at the proximal portion due to various factors, such as compliance of the EMD, friction against the vessel wall, tortuosity of the vasculature or resistance encountering a lesion, for example. For some robotic movements, it is possible to compensate for the mismatch and input or adjust the movement at the proximal portion to more closely achieve the desired movement at the distal end. For example, the magnitude of the movement desired at the distal end may be scaled by a factor which is applied to the actuated movement at the proximal end. The factor may be determined based on real-time imaging, experimentation, or historical data based on the procedure, device characteristics, the particular vasculature or other parameters. The factor or adjustment can be applied by the operator or by the control computing system.

Figure 4A:
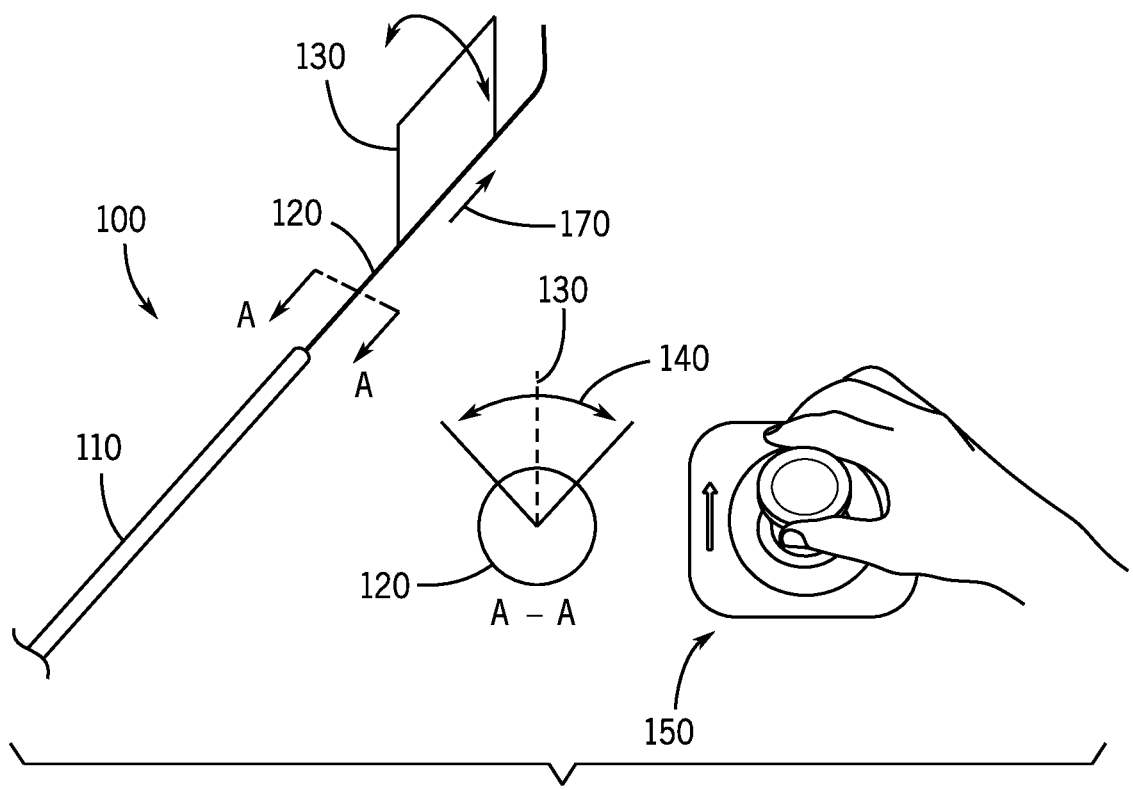
FIGS. 4A and 4B illustrate an example mode, referred to herein as wiggle, for a robotic movement of an elongated medical device (EMD) in a catheter-based procedure system.
Figure 4B:
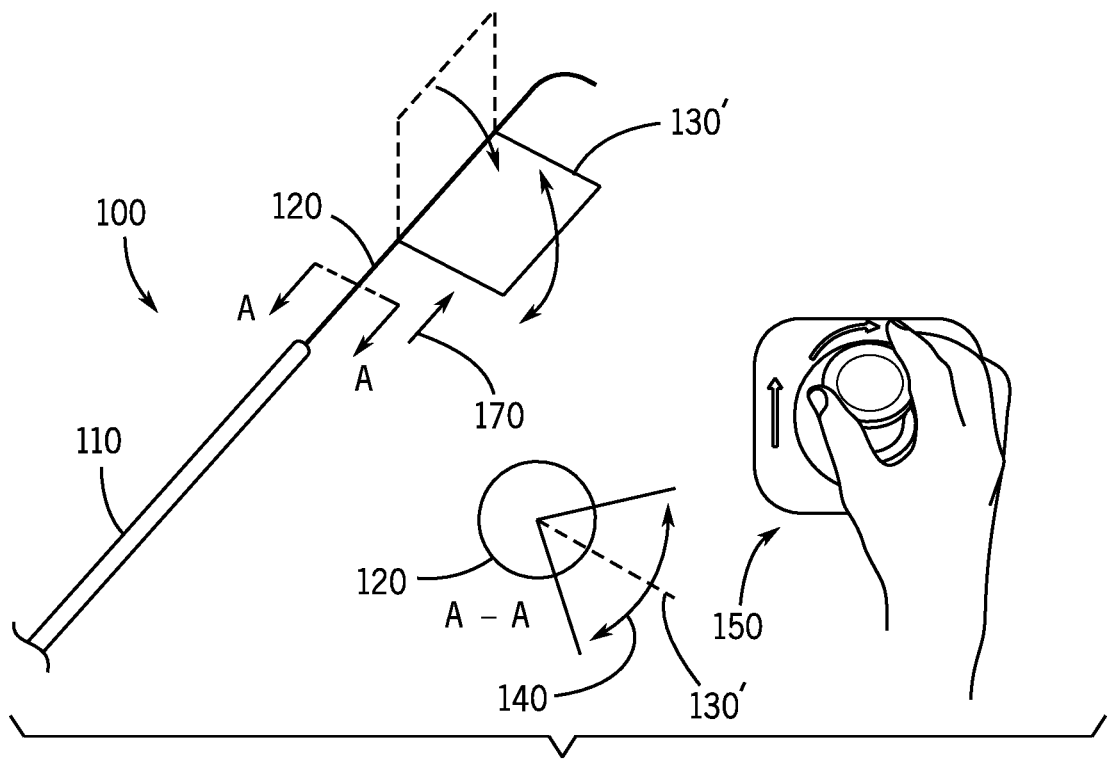

Referring now to FIGS. 4A and 4B, an example mode for a robotic movement in an EMD system is illustrated. FIGS. 4A and 4B illustrate an example EMD arrangement 100 that may be used in the example system described above with reference to FIGS. 1-3. The example EMD arrangement 100 includes a first EMD 110 and a second EMD 120. FIGS. 4A and 4B illustrate the distal portion of the EMDs 110, 120. The two EMDs are arranged in a co-axial manner with the second EMD 120 positioned within the first EMD 110. In this regard, the first EMD 110 has inner lumen which can accommodate the second EMD 120 and allows the second EMD to move (e.g., rotate and/or translate) within and relative to the first EMD 110. Of course, those skilled in the art will appreciate that, in other examples, more than two EMDs may be provided and arranged coaxially and that more than one EMD may be accommodated in the inner lumen of another EMD.

When the mode is selected by the operator, the robotic drive 24 causes one or more EMDs 110, 120 to enter a predetermined movement pattern. In the example illustrated in FIGS. 4A and 4B, one EMD (e.g., the guidewire) enters the predetermined movement pattern. In other examples, multiple EMDs may enter the pattern at a different times (e.g., one EMD at a time). The mode for robotic movement illustrated in FIGS. 4A and 4B is referred to herein as a wiggle mode. Wiggle mode is characterized by oscillating rotation of an EMD about its longitudinal axis. In one example, when the wiggle mode is enabled, an EMD (the second EMD 120 in the example illustrated in FIGS. 4A and 4B) enters into a rotational oscillation about the longitudinal axis 125. In another example, the EMD 120 only rotationally oscillates when the user commands the EMD 120 to advance with forward linear translation. In this regard, EMD 120, which is depicted as a guidewire, alternatively rotates in clockwise and counterclockwise direction, as indicated in the cross-sectional view A-A in FIG. 4A. The oscillation of an EMD may be characterized by various parameters, such as amplitude and/or frequency. As illustrated in FIG. 4A, the amplitude is indicated by the range of rotation 140 about a center position, represented in FIG. 4A by a reference plane 130. In various examples, an operator can configure the oscillation parameters, such as amplitude, rotational speed, frequency or cycle time.

The various parameters of the oscillation may be set in the predetermined pattern to achieve a desired result or for certain purposes. For example, the amplitude of the oscillation may be set to between about 60 degrees and about 180 degrees, preferably between about 90 degrees and about 150 degrees, and more preferably about 125 degrees. The cycle time (e.g., time to complete one oscillation) or the oscillation frequency may be similarly set in the predetermined pattern to achieve a desired result. In various examples, the oscillation of the EMD is performed at a rotational speed of 900 degrees per second.

As noted above, the various robotic movements may be implemented for various EMDs. The wiggle mode described above may be implemented for a guidewire for navigation, or advancing through a vessel, for example. The wiggle mode may be implemented with different parameters on the guidewire for purposes of crossing an obstacle, such as a lesion. In this regard, the amplitude of the oscillation is set to a greater level. For example, the amplitude of the oscillation for purposes of lesion crossing may be set at between about 180 and about 900 degrees, preferably between about 360 and about 720 degrees. With these parameters, the mode may be referred to as a "spin" mode and can be selected by the operator.

As illustrated in FIGS. 4A and 4B, an auxiliary command can be used to modify certain characteristics of the oscillation of the EMD. In the example illustrated in FIGS. 4A and 4B, the auxiliary command may be received from a user input device, such as a joystick 150. FIG. 4A illustrated the oscillation about the plane 130 representing the center position of the oscillation with no rotational input from the joystick 150. The joystick in FIG. 4A is illustrated with a forward input to cause forward linear translation of the EMD 120, as indicated by the arrow on the joystick and arrow 170 adjacent to EMD 120 in FIG. 4A. The oscillation may be modified through commands from the joystick 150.

In this regard, inputs from the joystick 150 can skew, or re-orient the center position of, the oscillation. For example, as illustrated in FIG. 4B, the center position of the oscillation can be moved by rotating the joystick. Rotating the joystick clockwise results in movement of the center position 130 clockwise to a new center position 130', as illustrated in FIG. 4B.

As noted above, other parameters of the oscillation can be modified by the operator, such as amplitude, frequency, rotational speed or cycle time. For example, the amplitude of the oscillation can be modified through a user input using the joystick or another input device, such as a graphical user interface. In the case of the joystick, the amplitude may be increased by rotating the joystick clockwise or reduced by rotating the joystick counterclockwise. In this regard, if the amplitude is set in the predetermined mode at 125 degrees, rotating the joystick clockwise can increase the amplitude to a higher value, such as 150 degrees. Similarly, rotating the joystick counterclockwise can decrease the amplitude to a lower value, such as 90 degrees.

FIGS. 4A and 4B illustrate the auxiliary command being received from an operator input device, such as the joystick 150. In other examples, the auxiliary command may be received from a controller or control module, such as the control computing system 34 described above with reference to FIG. 2. The control module may generate the auxiliary command in response to another user input or in response to a detected parameter, such as resistance to the movement or the movement of the distal portion of the EMD.

As noted above, in certain cases, the predetermined movement pattern of the wiggle mode is implemented for purposes of navigation. In this regard, the predetermined movement accompanies a forward linear movement of the EMD (e.g., the guidewire). Thus, while the mode may be enabled, the oscillation may be active only while the EMD is in forward linear movement. In various examples, when the forward linear movement is stopped for a predetermined time (e.g., 1 second), the rotational oscillation may be suspended. The rotational oscillation is not active during non-forward linear movement. Thus, the rotational oscillation may be suspended if the linear movement is reversed or jogged. In this regard, "jogged" refers to discrete movements (rotational or linear) of the EMD which are performed in response to inputs from the operator.

Figure 5:
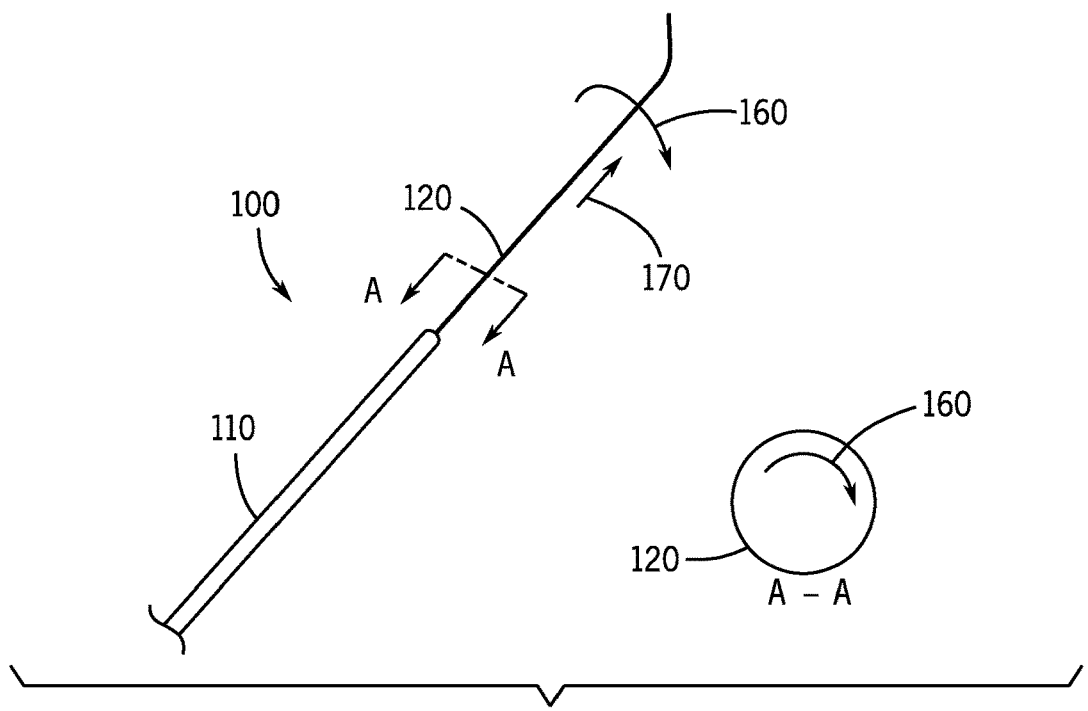
FIG. 5 illustrates another example mode, referred to herein as drill, for a robotic movement of an EMD in a catheter-based procedure system.

Referring now to FIG. 5, another example mode for a robotic movement in an EMD system is illustrated. FIG. 5 illustrates the example EMD arrangement 100 described above with reference to FIGS. 4A and 4B. The example EMD arrangement 100 includes the first EMD 110 and the second EMD 120 arranged in a co-axial manner, as illustrated in the cross-sectional view A-A.

FIG. 5 illustrates a predetermined movement pattern associated with a mode referred to herein as a drill mode. When the drill mode is selected by the operator, the robotic drive 24 causes one or more EMDs 110, 120 to enter the predetermined movement pattern characterized by continuous, unidirectional rotation of at least one EMD about its longitudinal axis 125, as indicated by the arrow 160, combined with forward linear movement of the EMD, as indicated by the arrow 170. In this regard, the EMD (e.g., the second EMD 120 or guidewire) spins in one direction. The direction of rotation may be clockwise or counterclockwise. The unidirectional rotation 160 of the EMD 120 may be characterized by a rotational speed. The rotational speed may be set as part of the predetermined movement pattern. For example, the rotational speed may be set at between about 1 and about 10 revolutions per second and, preferably, about 2.5 revolutions per second. In various examples, an operator can configure the rotational speed by inputting a different value.

As noted above, the various robotic movements may be implemented for various EMDs. The drill mode illustrated in FIG. 5 may be implemented for a guidewire for crossing an obstacle, such as a lesion.

As with the wiggle mode described above with reference to FIGS. 4A and 4B, with the drill mode of FIG. 5 enabled, when the forward linear movement is stopped for a predetermined time, the continuous unidirectional rotational may be suspended. Thus, while the drill mode may be enabled, the rotation may be stopped while the EMD in not in forward linear movement. A similar suspension of the unidirectional rotation may be implemented if the linear movement is reversed or jogged. In various examples, an auxiliary input may be used to increase or decrease the rotational speed during the drill mode. For example, the operator may move the joystick forward to increase the rate and reverse to reduce the rate of rotation.

Figure 6:
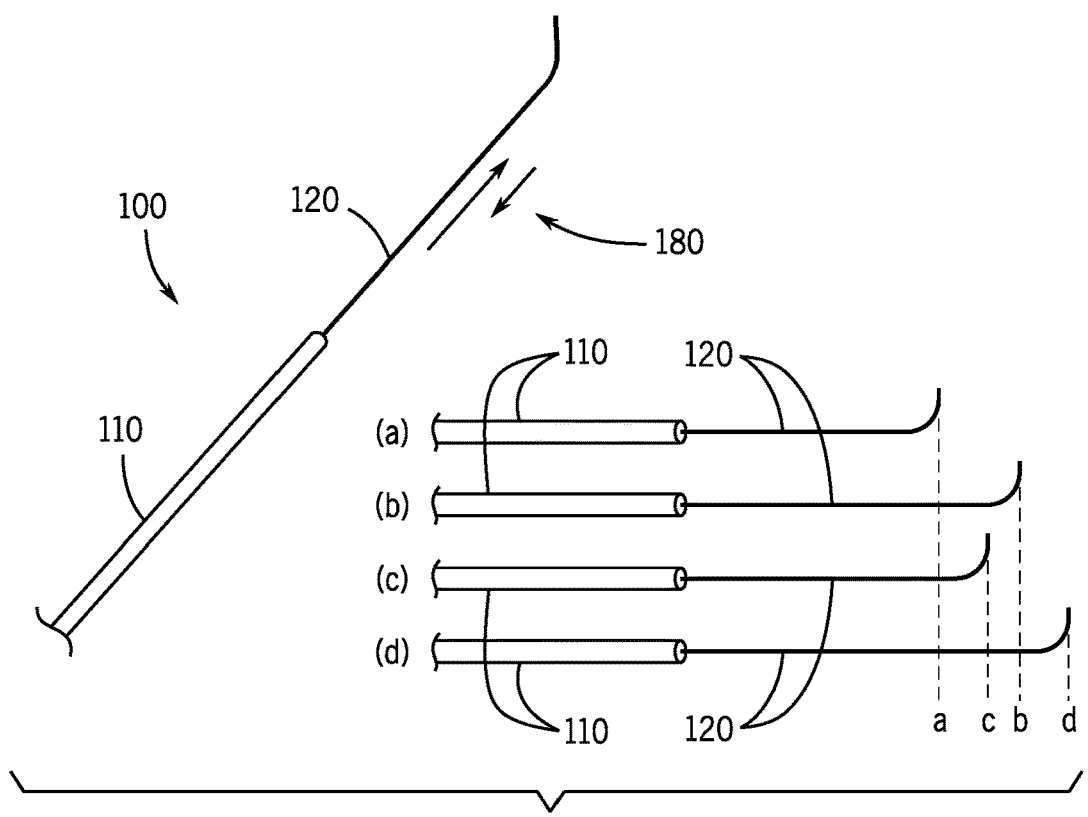
FIG. 6 illustrates various phases of another example mode, referred to herein as jackhammer, for a robotic movement of an EMD in a catheter-based procedure system.

Referring now to FIG. 6, various phases of another example mode for a robotic movement in an EMD system are illustrated. FIG. 6 illustrates the example EMD arrangement 100 described above with reference to FIGS. 4A, 4B and 5. The example EMD arrangement 100 includes the first EMD 110 and the second EMD 120 arranged in a co-axial manner.

FIG. 6 illustrates a predetermined movement pattern associated with a mode referred to herein as a jackhammer mode. When the jackhammer mode is selected by the operator, the robotic drive 24 causes one or more EMDs 110, 120 to enter the predetermined movement pattern characterized by linear oscillation of the EMD 110, 120. In the example illustrated in FIG. 6, the second EMD 120 (e.g., guidewire) is shown as being in linear oscillation. The jackhammer mode may be used by an operator to facilitate crossing of an obstacle, such as a lesion, by the guidewire.

As illustrated in FIG. 6, the linear oscillation includes alternating forward and reverse linear movement of the elongated medical device. FIG. 6 illustrates forward linear movement of the EMD 120 from the position (a) to the position (b), followed by reverse linear movement of the EMD 120 from the position (b) to the position (c). The movement pattern continues with repeating of the cycle, stating with movement of the EMD 120 from the position (c) to the position (d).

The jackhammer mode illustrated in FIG. 6 performs the alternating forward and reverse linear movement of the elongated medical device with a resultant forward linear movement of the EMD 120, allowing the EMD 120 to traverse or cross a lesion, for example. In this regard, the alternating forward linear movement is at least slightly larger than the alternating reverse linear movement. Thus, as illustrated in FIG. 6, at the start of an oscillation cycle, the EMD 120 is at position (a), and the end of the oscillation cycle (and the start of the next oscillation cycle), the EMD 120 is at position (c), which is forward of the position (a). Thus, the cumulative forward linear movement allows the EMD 120 to traverse or cross a lesion, for example.

As noted above and illustrated in the example of FIG. 6, the jackhammer mode is used with the second EMD 120, or the guidewire. In other example, a similar pattern of movement may be used with other EMDs, such as the microcatheter (or the first EMD 110).

As with the wiggle mode and the drill mode described above with reference to FIGS. 4A, 4B and 5, with the jackhammer mode of FIG. 6 enabled, when the input for forward linear movement is stopped, the alternating forward and linear movement characterizing the jackhammer mode may be suspended. In one example, the jackhammer mode may be suspended when the input for forward linear movement is stopped for a predetermined time. Thus, while the jackhammer mode may be enabled, the linear oscillation may be stopped while the EMD in not in forward linear movement. A similar suspension may be implemented if the linear movement is reversed or jogged.

Figure 7:
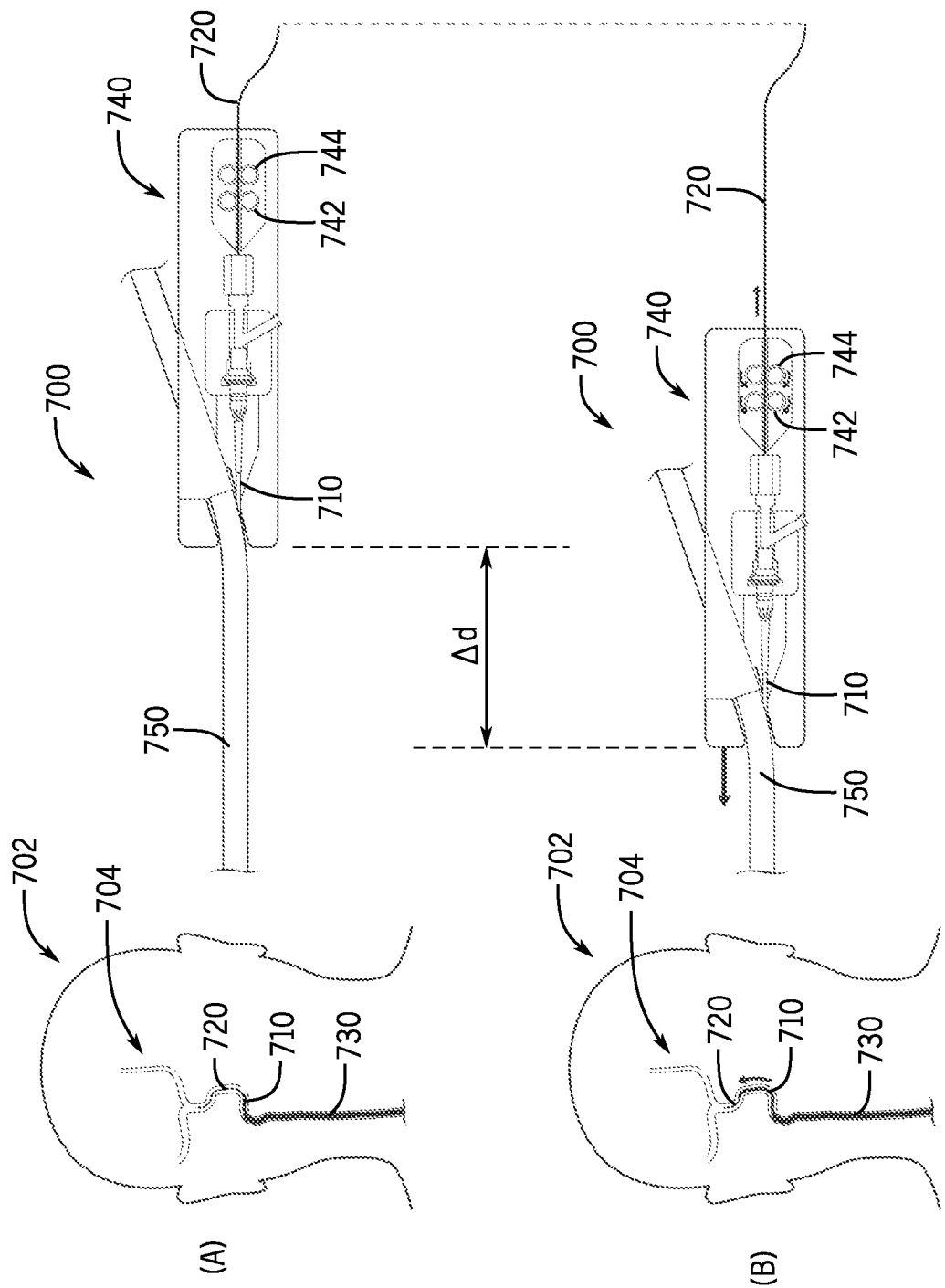
FIG. 7 illustrates another example mode, referred to herein as active device fixation (ADF), for a robotic movement of an EMD, in a catheter-based procedure system.

Referring now to FIG. 7, another example mode for a robotic movement in an EMD system is illustrated. The mode illustrated in FIG. 7 is referred to as active device fixation (ADF). ADF may be enabled in a system in which at least two EMD's are used for a procedure in an apparatus such as robotic system 700 in which the device module for an EMD 720 is coupled to the device module 740 of another EMD 710. In the example of FIG. 7, a robotic system 700 is used to perform a procedure on a patient 702 by inserting EMDs into vasculature 704 of the patient 702.

The robotic system 700 of FIG. 7 includes a first EMD, such as a microcatheter 710, and a second EMD, which is a guidewire 720. A third EMD, such as a guide catheter 730, is provided to allow the microcatheter 710 and the guidewire 720 to be translated therethrough. The microcatheter 710 is translated linearly through corresponding linear translation of a device module 740, which includes a device support, or support track 750, through which the EMDs 710, 720 are coaxially fed to the next device module.

In the arrangement illustrated in FIG. 7, the device module translates linearly, driving a linear translation of the microcatheter 710. The translation of device module 740 will also drive linear translation of guidewire 720. The guide catheter 730 may be translated linearly by additional corresponding device module (not shown in FIG. 7). The microcatheter 710, the guidewire 720, and the guide catheter 730 are in co-axial formation. Thus, as illustrated in FIG. 7, within the patient 702, the three EMDs 710, 720, 730 are positioned coaxially through a passage, such as the internal carotid artery.

An operator may wish to reposition one EMD while another EMD remains stationary within the patient 702. For example, the operator may wish to linearly translate the microcatheter 710, while maintaining the position of the guidewire 720, to the positions illustrated in FIG. 7B. FIG. 7 illustrates the positions of the distal portions of the EMDs 710, 720, 730. Of course, those skilled in the art will understand that, as described above, it is the proximal end of the EMDs that is controlled.

With the ADF mode enabled, the operator can linearly translate the microcatheter 710 by translating the device module 740 forward by a distance Ad, as illustrated in FIG. 7B. In various examples, the measurement of the movement via an encoder is used to make the determination of magnitude and direction. The ADF mode causes a corresponding movement of the guidewire 720 in the opposite direction, resulting in the position of the proximal end of the guidewire 720 to remain substantially stationary relative to the patient 702, as illustrated in FIG. 7.

Movement of the guidewire 720 relative to the device module 740 can be implemented through the use of drive tires 742, and the linear movement of the guidewire 720 can be measured using corresponding an encoder which may be coupled to auxiliary encoder tires 744. As illustrated in FIG. 7B, the drive tires 742 cause a backward translation of the guidewire 720 relative to the device module 740. If the microcatheter were retracted, then the drive tires 742 would cause a forward translation of the guidewire 720 relative to the device module 740. The rotation of the auxiliary encoder tires 744 by the movement of the guidewire 720 is provided to a central controller, such as the control computing system 34 described above with reference to FIG. 2.

In response to the determined translation of the first EMD 710, with the ADF mode enabled, the control computing system 34 can cause a linear translation of the guidewire 720 with a substantially equal magnitude to the linear translation of the microcatheter 710 (Ad in the example of FIG. 7) and in a direction opposite the direction of translation of the microcatheter 710 relative to the device module 740.

Figure 8:
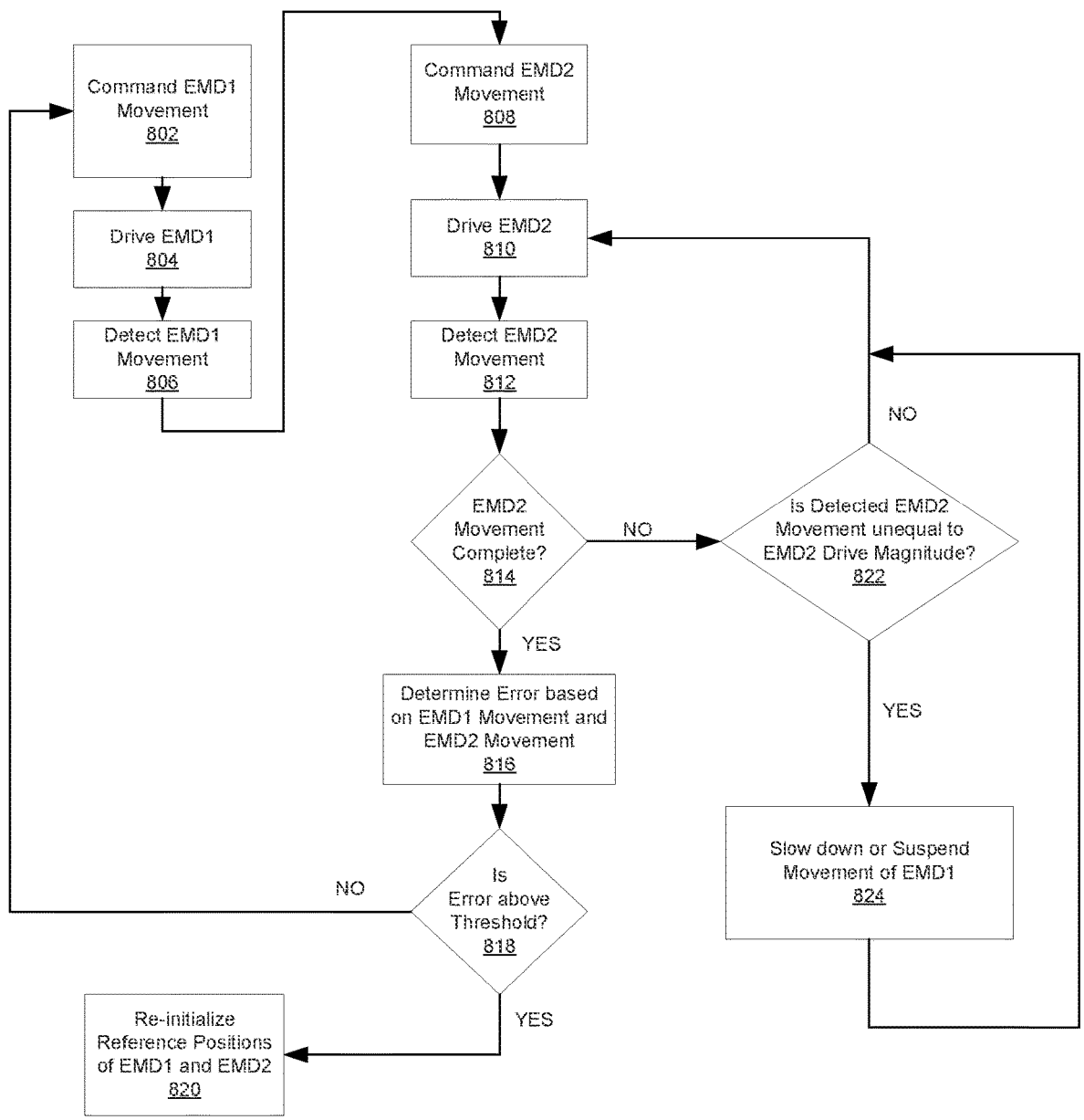
FIG. 8 is a flowchart illustrating a method for closed-loop operation associated with the example mode of FIG. 7.

Referring now to FIG. 8, a flowchart illustrates an example method 800 of the implementation of the ADF mode using a closed-loop operation. In accordance with the example of FIG. 8, the process begins with a movement of the first EMD (e.g., the microcatheter 710) being commanded, which may be performed by the operator (block 802). In response to the command, the microcatheter 710 is driven by the device module 740 (block 804). The movement of the microcatheter 710 may be detected (or determined) based on, for example, indication from an encoder that tracks the position of the microcatheter 710 (block 806).

Based on the determination of the movement of the microcatheter 710, a corresponding movement of the second EMD (e.g., guidewire 720) in the opposite direction is commanded (block 808). The commanded movement of the second EMD 720 is effected through driving of the guidewire 720 by, for example, the drive tires 742 (block 810). Movement of the guidewire 720 is detected by, for example, an encoder coupled to the auxiliary encoder tires 744 or other sensors provided in the system 700 (block 812).

In the example of FIG. 8, various safety features are provided to provide safeguards in the closed-loop operation. The safeguards may prevent against over-correction or mis-correction due to failure or defect in the sensors (e.g., encoder) or the drive tires 742.

In this regard, at block 814, the control computing system may determine whether the desired movement of the guidewire 720 (e.g., the movement responsive to the movement of the microcatheter 710) has been completed, as may be indicated by the guidewire 720 reaching a desired target position. In this regard, the control computing system may use the amount of movement measured by the associated encoders 742. If the amount of movement as measured by associated encoders is substantially equal to the desired movement of the guidewire 720, the movement is deemed complete at block 814, and the process moves to block 816. At block 816, the difference between the measured movement of the microcatheter 710 (at block 802) and the measured movement of the guidewire 720 through the encoder is calculated as an error. If the error is below a threshold (for example 0.5 mm), the process is considered complete and returns to block 802 for a new commanded movement of the first EMD 710. In some examples, the error determined at block 816 may be added to previous errors, and the error compared to a threshold is a cumulative threshold.

At block 814, the compensating movement of the guidewire 720 may be determined to be complete if the guidewire 720 position is within a first error threshold. The first threshold is the difference between the microcatheter 710 change in position and the equal and opposite change in the position of the guidewire 720. For example, once the difference in the movements is within 0.5 mm of each other, the movement may be deemed complete. Without this first threshold, the guidewire 720 will continue to move to correct the position error and may oscillate. The operator may find this oscillation to be undesirable when positioning an EMD in the patient's anatomy. In some cases, the compensating movement of the guidewire 720 can resume if the position error becomes greater than a second threshold which is greater than the first threshold. For example, the compensating movement does not resume again unless the position error becomes greater than a second threshold of 1.0 mm. In another example, the compensating movement may resume upon further command input (for example from the user actuating a joystick).

Returning again to block 814, if the movement of the guidewire 720 has not completed the movement commanded in response to the movement of the microcatheter 710, the process determines whether the detected movement of the guidewire 720 is unequal to the magnitude of the movement of the guidewire 720 commanded via the tires. This may occur if the amount of commanded movement of the drive tires does not match the detected movement of the encoder tires. In this case, the ADF mode may limit the amount of driving by the drive tires to prevent over-translation of the guidewire 720 in the event that the mismatch is due to a failure in the sensor (encoder tires).

In other examples, input from the encoder 734 may indicate that the movement of the guidewire 720 is unable to keep up with the movement of the microcatheter 710, as may result from slipping or loss of traction between the drive tires 742 and the guidewire 720. So that the guidewire's proximal position is maintained when the movement of the guidewire 720 is unable to keep up with the movement of the microcatheter 710, the movement of the microcatheter 710 may be slowed or stopped.

In the example of FIGS. 7 and 8, the linear motion of the first EMD 710 and the second EMD 720 are substantially simultaneous. Of course, those skilled in the art will appreciate that the timing of the processor or the frequency of measurements may result in a minimal offset in the timing of the movements.

In one example, data from the encoder may indicate an unintended movement of an EMD 710, 720. The movement may be determined to be unintended if it exceeds a predetermined speed or threshold, for example, or does not correspond to a commanded movement. In such an event, the movement may be recognized as unintended, and the reference positions of the EMDs 710, 720 may be adjusted without any modification to the speed or magnitude of the commanded translation of either EMD.

Data from the encoder coupled to the auxiliary encoder tires 744 may be used to detect the presence or absence of the second EMD 720. For example, when movement of the guidewire 720 is commanded through movement of the drive tires 742, signals from the auxiliary encoder tires 744 can be used to indicate the presence or absence of the guidewire. If the auxiliary encoder tires 744 indicate a movement of the guidewire 720 over a certain threshold (for example 0.1 mm) which corresponds to the commanded movement, presence of the guidewire 720 can be confirmed. On the other hand, if there is no movement detected by the auxiliary encoder tires 744 in response to commanded movement of the drive tires 742, absence of the guidewire 720 may be detected or determined. In another example, the second EMD 720 can be assumed to not be present by the control computing system until its presence is first able to be detected.

Those skilled in the art will appreciate that the number of EMDs may be greater than two. For example, in the examples described above, one or more additional EMDs (in addition to the guidewire 720) may be translated in response to the movement of the microcatheter. For example, EMDs translated in response to the movement of the microcatheter may include a guidewire, a balloon or stent catheter and possibly additional EMDs. In one example one or more additional EMDs are included the behavior of each is constrained in the same manner as the second EMD. For example, where the guide catheter is moved multiple EMDs are moved in equal and opposite directions of movement of the guide catheter. In one system a guide catheter and guidewire and a third EMD are positioned on a common base that moves all three devices together. To maintain the position of the guidewire and third EMD relative to a patient the guidewire and third EMD move in an opposite direction to movement of the base equal and opposite to movement of the guide catheter. Where there are multiple EMD devices the device that is not keeping up the in the opposite direction relative to the guide catheter is the EMD that constrains the guide catheter's movement. Stated another way the guide catheter is constrained (slowed down or stopped) by the EMD that is lagging the most of the other EMDs. The other EMDs will continue to track the movement of the guide catheter. The result is that all EMDs will move a distance substantially equal and opposite to the distance moved by the guide catheter.

Figure 9:
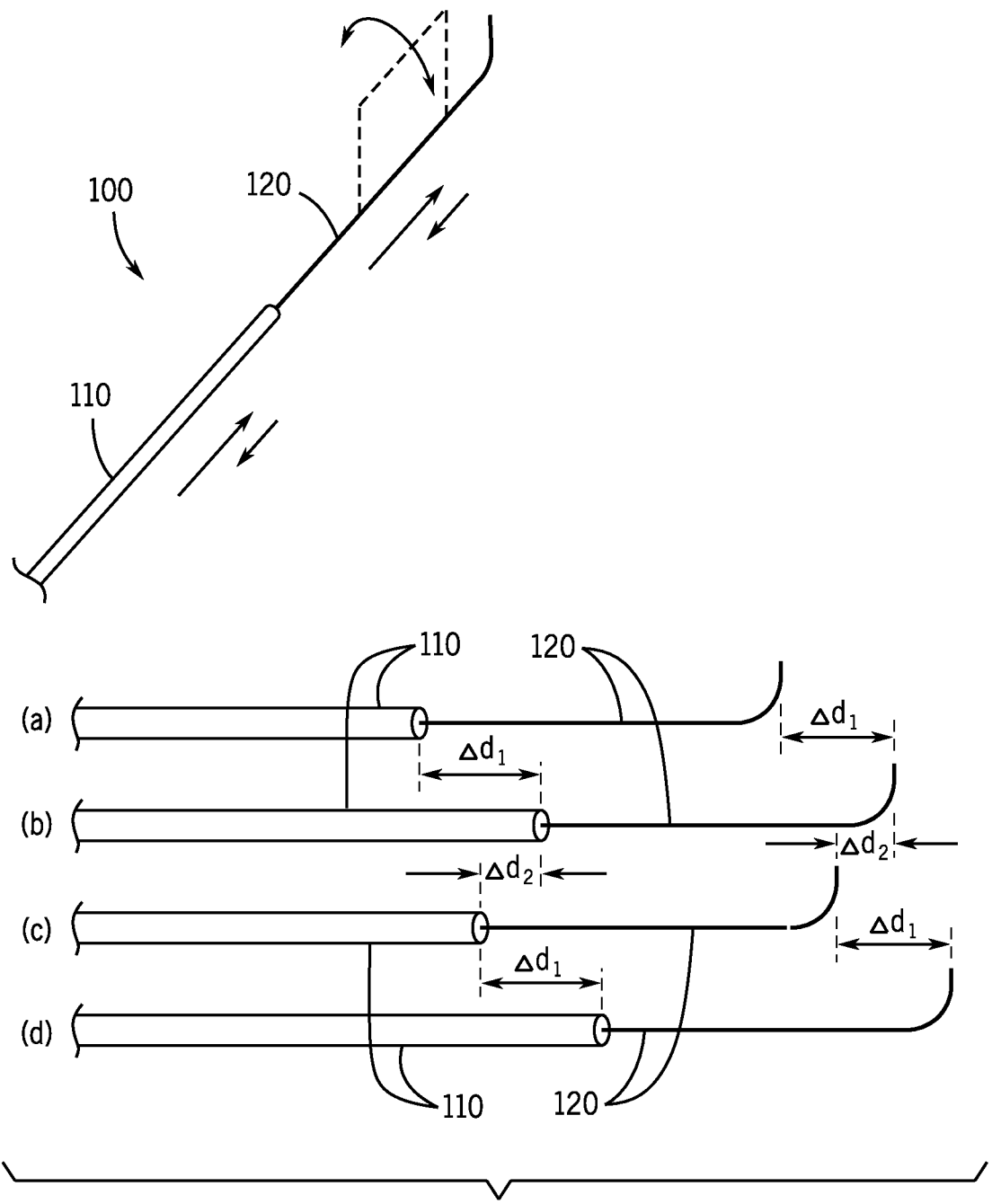
FIG. 9 illustrates another example mode for synchronized robotic movement of two or more EMDs in a catheter-based procedure system.

Referring now to FIG. 9, another example mode for a robotic movement in an EMD system is illustrated. The closed-loop operation described above with reference to FIGS. 7 and 8 may be used to synchronize movement of two or more EMDs where at least two EMDs are driven by independent drive modules. In the example illustrated in FIG. 9, the EMDs 110, 120 are moved in synchronous manner in a jackhammer mode described above with reference to FIG. 6.

As illustrated in FIG. 9, the linear oscillation associated with the jackhammer mode includes alternating forward and reverse linear movement of the two EMDs 110, 120. FIG. 9 illustrates forward linear movement of the EMDs 110, 120 from the position (a) to the position (b) each by a magnitude of $\Delta d_1$, followed by reverse linear movement of the EMDs 110, 120 from the position (b) to the position (c) each by a magnitude of Adz. As noted above, the magnitude of the forward linear movement ($\Delta d_1$) is greater than the magnitude of the reverse linear movement (Adz). The movement pattern continues with repeating of the cycle, starting with movement of the EMDs 110, 120 from the position (c) to the position (d), again each by a magnitude of $\Delta d_1$.

The synchronization of the movements of first EMD 110 and the second EMD 120 may be achieved through a closed-loop system which uses inputs from sensors, such as an encoder, to detect or determine movement of one EMD and use the information from the sensors to drive another EMD. For example, a command may cause driving of the first EMD 110. The command may be received from a controller or an operator input. Encoder tires, such as the auxiliary encoder tires 744 described above with reference to FIG. 7, can be used to measure the movement of the first EMD 110. In response to the measured movement of the first EMD 110, the controller may cause the second EMD 120 to be driven for translation by the same magnitude and same direction as the first EMD 110.

Figure 10:
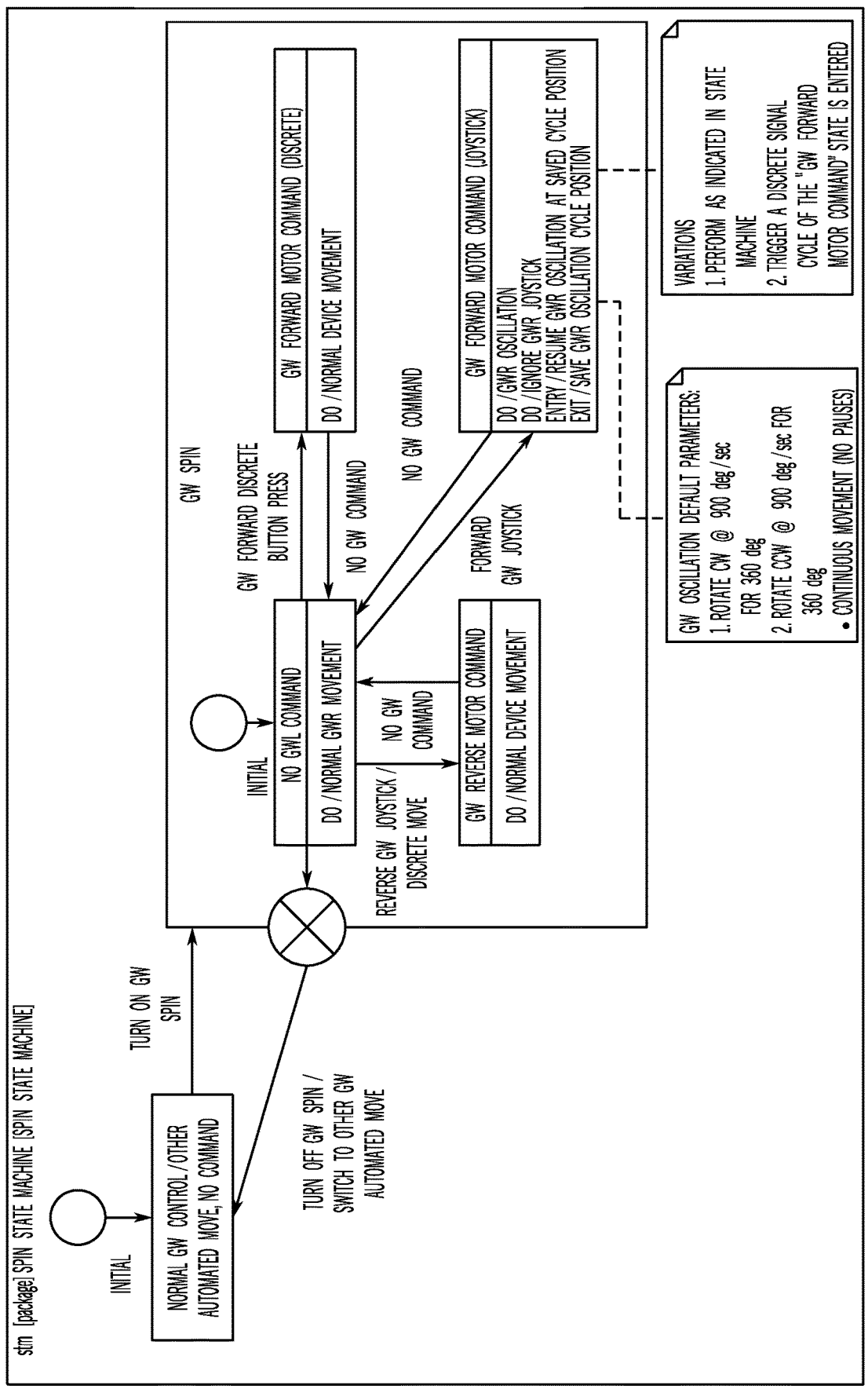
FIGS. 10 and 11 are state machine command diagrams associated with example mode of FIGS. 4A and 4B.

Referring to FIG. 10, a state machine diagram corresponding to one example of the wiggle mode referred to above as the spin mode described above with reference to FIGS. 4A and 4B. The example of FIG. 10 illustrates how commands are provided to the primary user input and the linear drive and rotational drive for the guidewire device. Once the spin mode is selected, a rotational drive mechanism provides rotational oscillation of the guidewire while the guidewire is being driven forward. Referring to FIG. 10, when the selected example of the spin mode has been selected, there are four different command states. First, in a No GWL (guidewire linear) command state where there is no command from the primary user input then the controller provides no automatic instruction to the rotational drive mechanism or the linear drive mechanism to provide rotational or linear movement to the guidewire. In this state an operator may provide rotational movement to the guidewire (GW) by rotational movement of the user input. Second, in the GW forward motor command state when the operator provides a command via the primary user interface to move the guidewire in a linear forward direction the rotational drive automatically provides rotary oscillation movement to the guidewire. Further, in the GW forward motor command state, any rotational input to the primary user input will be ignored, and no additional rotational movement will be imparted to the guidewire from the rotational drive. In this GW forward motor command state, where the primary user interface is a joystick, if the operator rotates the joystick, that would provide clockwise (CW) and counterclockwise (CCW) rotational instructions to the rotational drive mechanism, the rotation of the joystick will result in no instruction from the controller to the rotational drive mechanism to rotate the guidewire in addition to the automatic oscillation of the guidewire. In a third command state, GW reverse motor, where a user provides a linear reverse movement command through the primary user input, the guidewire rotational drive will not provide any rotational movement to the guidewire unless the user also provides an instruction to rotate the guidewire. Where the primary user input is a joystick movement of the joystick in rearward direction will provide an instruction to the linear drive to move the guidewire in reverse or withdrawal from a patient direction while providing no instruction to the rotational drive to provide rotational oscillating movement to the guidewire. However, in this third state any rotation of the CW or CCW movement of the joystick will result in the controller providing an instruction to the rotational drive to rotate the guidewire in a respective CW or CCW direction. Stated another way in this third state the reverse movement of the primary input behaves the same as in the base operating state. Where an operator ceases providing a linear forward instruction through the primary user input mechanism the location in oscillation cycle is saved and resumes the cycle from where it was stopped once the operator manipulation of the primary user input in the linear forward directions continues again. In one embodiment the position within the cycle is not saved and begins a new each time the operator stops and starts the linear forward motion via the primary user input.

In one example, the automatic rotational oscillation that does occur as outlined above in the various states is each cycle includes a first 900 deg/sec for 360 degree CW rotation and 900 deg/sec for 360 degree CCW rotation and then the cycle repeats without a pause between changes of direction other than that required by the physical limitation of the electro mechanical rotational drive mechanism. Of course, other speeds and amount of rotation are contemplated. In one example, the speed is between is less than 900 deg/sec and greater than 900 deg/sec.

In a fourth GW forward motor command (discrete) state, where the discrete movement mode has been selected by selecting a jog button for discrete forward movement, no rotational movement instruction is provided to the rotational drive mechanism. Once the user deselects the spin movement algorithm via the second user interface, operation of the primary user input reverts to the base standard instructions without any automatic alternating rotational movement.

Where the primary user input is a joystick, the controller and the spin movement technique is selected with a second user input, then the rotational drive mechanism will provide a rotational oscillation of a GW continuously during forward movement of the EMD using the primary controller. However, if the operator attempts to rotate the primary user input (such as a joystick) while the GW is moving forward, the system will not provide any additional rotation other than the rotational oscillation. In one embodiment the rate of oscillation may be degrees of rotation per unit of axial movement traveled or some other non-linear relationship between oscillation speed and liner speed.

In one example, no oscillating rotational movement is provided in the linear deadband of the primary user input. That is if the linear deadband is 2-3 degrees of movement of the primary user input, the automatic rotational oscillation will not occur until the primary user input is moved beyond the linear deadband. In one example, rotation of the primary user input without a linear movement instruction outside of the linear deadband will result in the rotational drive providing rotational movement to the guidewire.

Figure 11:
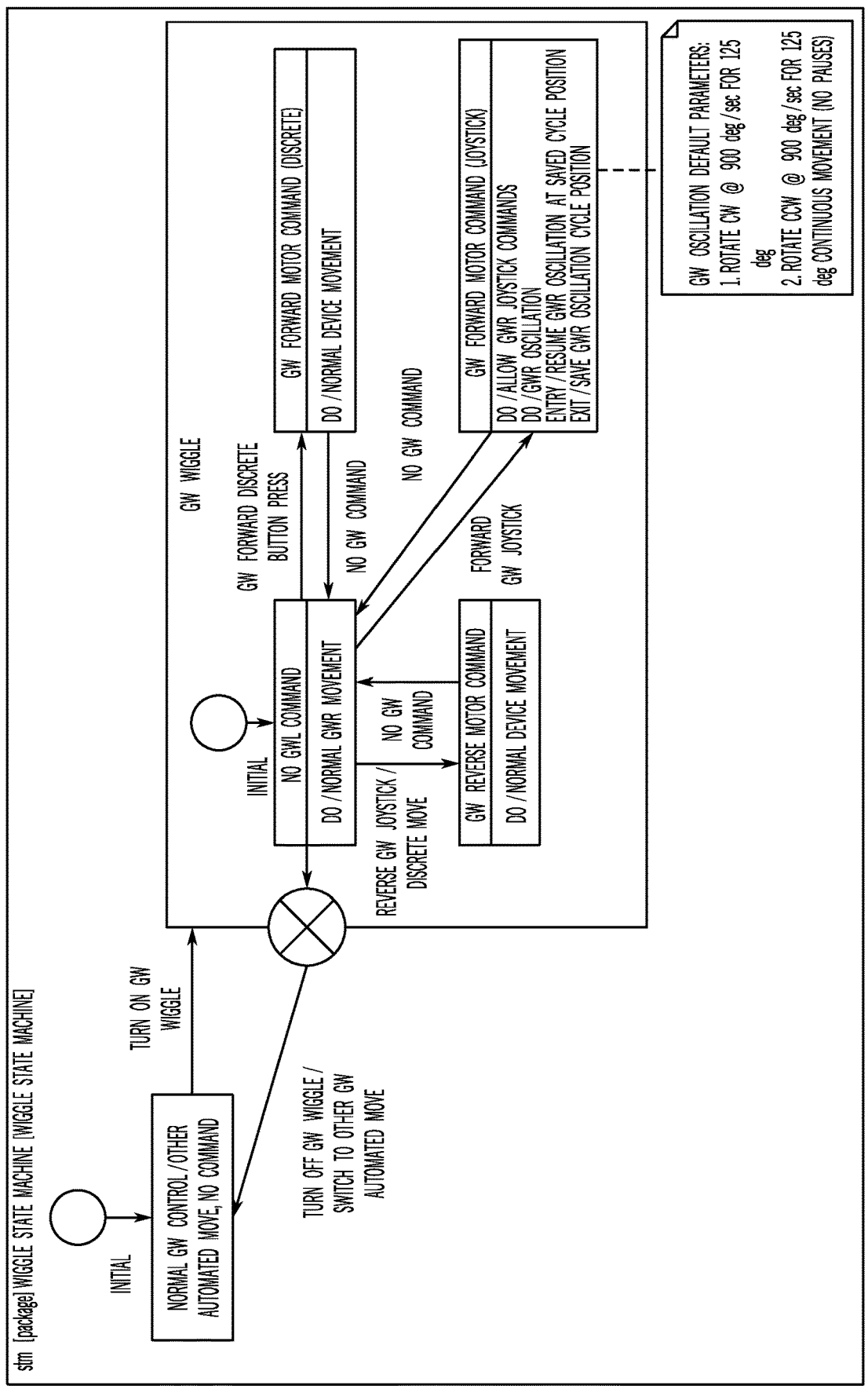

Referring to FIG. 11, a state machine diagram is provided corresponding to another example of the wiggle mode described above with reference to FIGS. 4A and 4B. The example illustrated in FIG. 11 has the same functionality as the example of FIG. 10 for the four states identified with the exception that a rotational input through the primary user input during rotational oscillation will result in the oscillation having a greater rotational movement in one direction than the other. By way of example where the primary user input is a joystick and the user is providing both a linear forward instruction to the linear drive mechanism by moving the joystick in a direction generally away from the user and simultaneously rotating the joystick in a clockwise direction the rotational drive mechanism will alternatively rotate the guidewire in a CW and CCW direction with the CW degree of rotation being greater than the CCW degree of rotation for each cycle. The further from a neutral position of the joystick the operator rotates the joystick the greater the ratio of CW to CCW rotation will be. Similarly, if the user rotates the joystick CCW while also moving the joystick in the forward direction the rotational drive will rotate the guidewire in a net CCW direction similarly to as described above.

Figure 12:
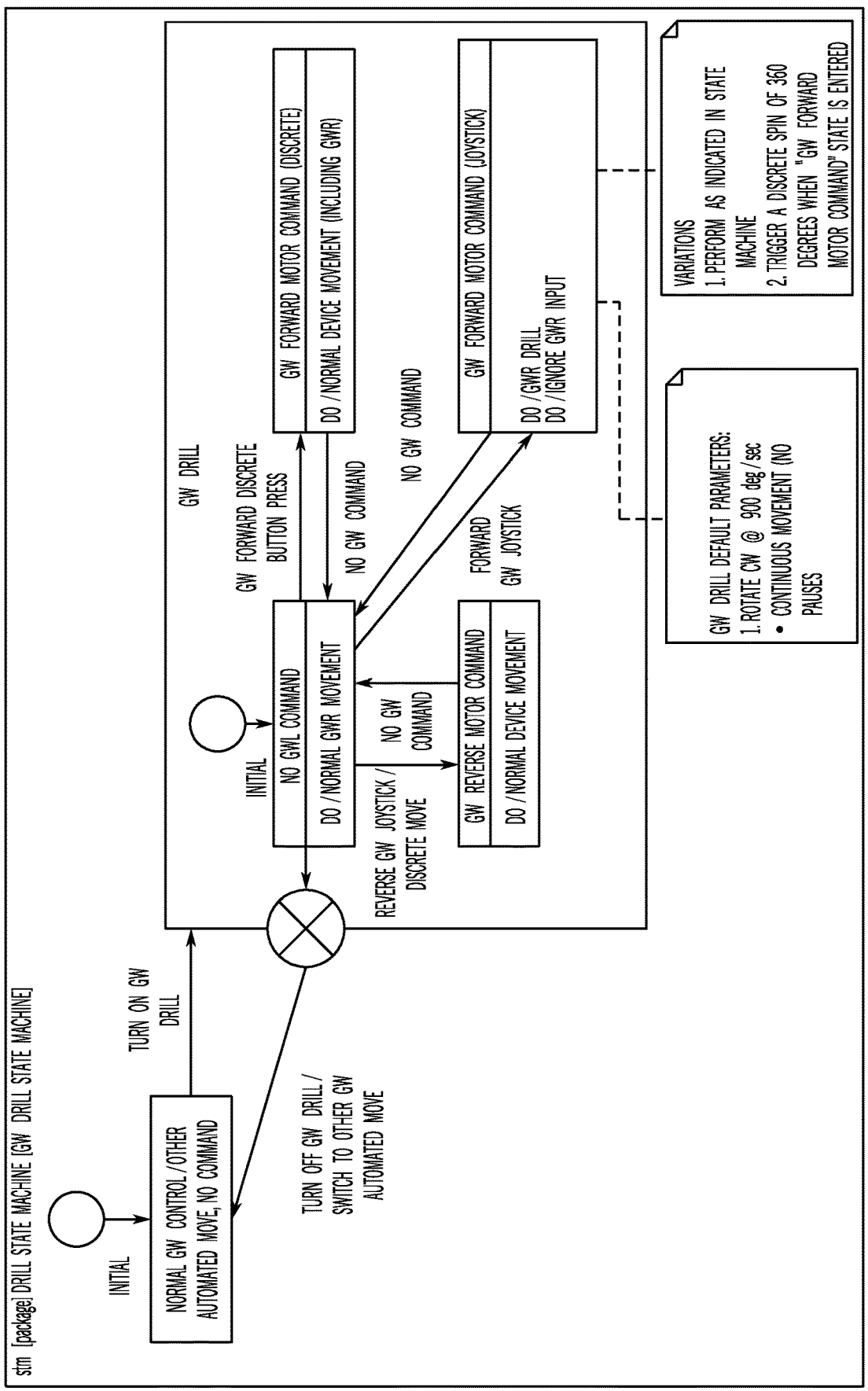
FIG. 12 is a state machine command diagram associated with example mode of FIG. 5.

Referring to FIG. 12, a state machine diagram is provided corresponding to an example of the drill mode described above with reference to FIG. 5. When the drill mode is selected, there are four different command states. First, in a No GWL (guidewire linear) command state where there is no guidewire linear command from the primary user interface, it is possible to provide normal CW and CCW rotational command through CW and CCW manipulation or movement of the primary user interface such as a joystick. That is an instruction from the primary user interface for CW or CCW rotation of the guidewire provides instructions via a controller to the rotational drive mechanism to rotate the guidewire in the CW or CCW direction. Second, in the GW forward motor command state when the operator provides a command via the primary user interface to move the guidewire in a linear forward direction the rotational drive automatically provides CW rotary movement to the guidewire. Further, in the GW forward motor command state, any rotational input to the primary user input will be ignored and no additional rotational movement will be imparted to the guidewire from the rotational drive. Where the primary user interface is a joystick if the operator attempts to rotate the joystick that would provide CW and CCW rotational instructions to the rotational drive mechanism in the second GW Forward Motor command state the rotation of the joystick will result in no instruction from the controller to the rotational drive mechanism to rotate the guidewire in addition to the automatic CW rotation of the guidewire. In a third GW reverse motor command state where a user provides a linear reverse movement command through the primary user input, the guidewire rotational drive will not provide any automatic rotational movement to the guidewire. If, however, in this state the user also provides an instruction to rotate the guidewire by manipulation of the primary user input then the GW will be rotated as in a base normal operating state. Where the primary user input is a joystick movement of the joystick in rearward direction will provide an instruction to the linear drive to move the guidewire in reverse or withdrawal from a patient direction while providing no instruction to the rotational drive to provide rotational movement to the guidewire. However, in this third state any rotation of the CW or CCW movement of the joystick will result the controller providing an instruction to the rotational drive to rotate the guidewire in a CW or CCW direction. Stated another way in this third state the reverse movement of the primary input behaves the same as in a base operating state.

In one example, the automatic rotational movement that does occur as outlined above in the various states is 900 deg/sec CW rotation. Of course, other speeds and rotational rates are contemplated. In one embodiment the speed is greater than 900 deg/sec and in one embodiment the speed is less than 900 deg/sec but greater than zero deg/sec.

In a fourth GW forward motor command (discrete) where the discrete movement mode has been selected by selecting a jog button for discrete forward movement, no rotational movement instruction is provided to the rotational drive mechanism. Once the user deselects the drill mode, operation of the primary user input reverts to the base standard instructions without any automatic rotational movement.

In one embodiment the rate rotation may be degrees of rotation per unit of axial movement traveled or some other non-linear relationship between rotational speed and linear speed.

In one example, while in the drill mode, no CW rotational movement is provided in the linear deadband of the primary user input. That is if the linear deadband is 2-3 degrees of movement of the primary user input, the automatic CW rotation will not occur until the primary user input is moved beyond the linear deadband. In one embodiment rotation of the primary user input without a linear movement instruction outside of the linear deadband will result in the rotational drive providing rotational movement to the guidewire.

Figure 13:
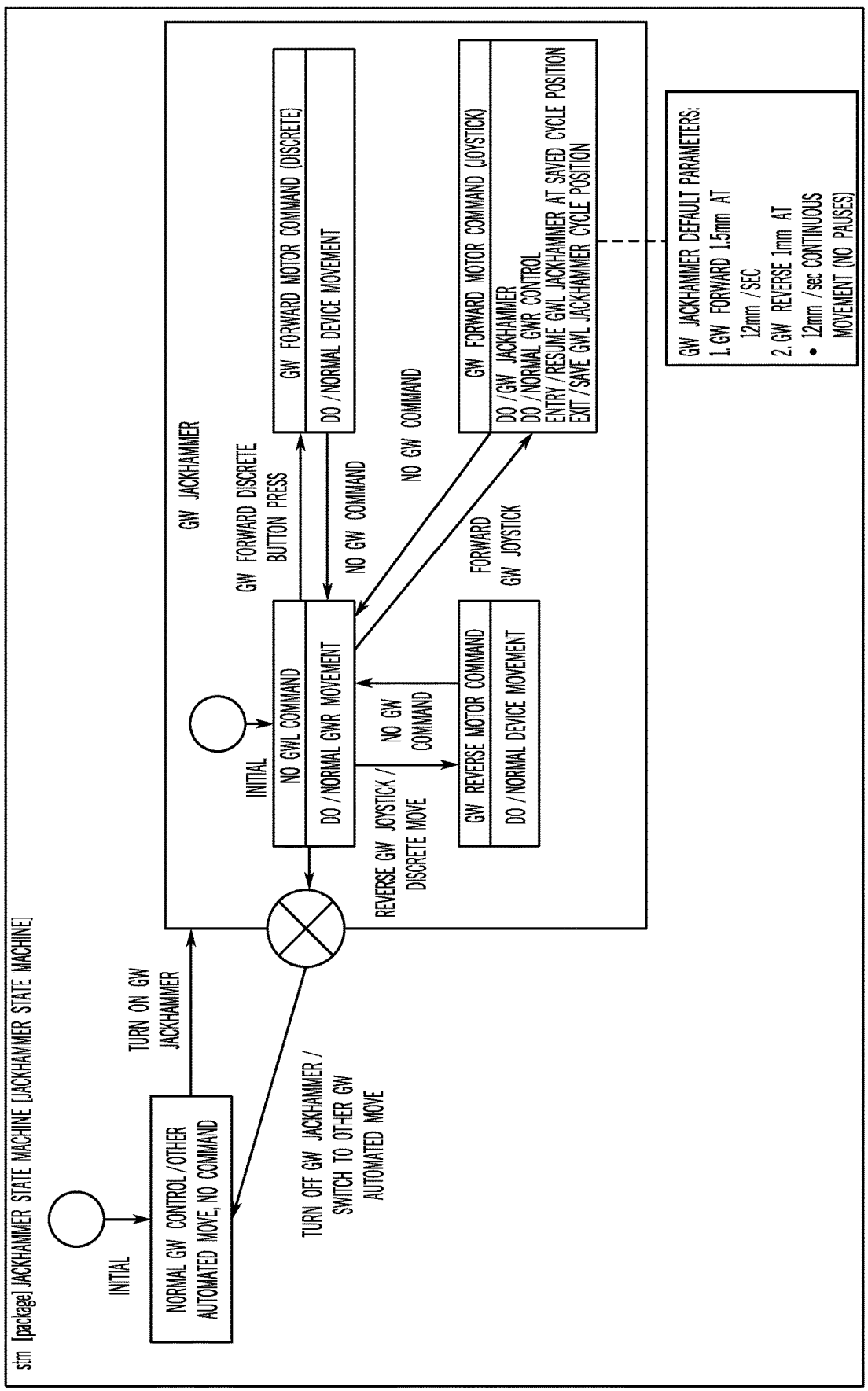
FIGS. 13 and 14 are state machine command diagrams associated with example mode of FIG. 6.

Referring now to FIG. 13, a state machine diagram is illustrated corresponding to one example of the jackhammer mode described above with reference to FIG. 6. In the example of FIG. 13, the jackhammer mode is applied to the guidewire. When the jackhammer mode for the guidewire (GW) is selected, there are a number of states that effect the movement of the GW. In a no GWL command state (no guidewire linear movement command) the user input provides normal rotational operation of the GW that is an operator may rotate the GW CW or CCW by manipulation of the user input. In the GW forward motor command (joystick) the GW linear drive mechanism automatically moves the GW in a cyclical forward and reverse direction with the forward movement being greater than the reverse movement. In this state the operator may also provide a CW or CCW direction to the GW by manipulation of the user interface (such as by rotating in a CW or CCW direction a joystick where the user interface is a joystick). In a GW reverse motor command state in which an operator manipulates the user interface to withdraw or provide a reverse movement to the GW there will be no automatic cyclical linear movement (forward and reverse) of the GW. In a GW forward motor command based on a jog or discrete movement button or input, the GW linear drive mechanism will not provide automatic cyclical linear movement to the GW. In one embodiment the automated cyclical movement is 1.5 mm forward at 12 mm/sec and 1 mm reverse at 12 mm/sec where the pause between the forward and reverse movement is the dwell period required by GW linear drive mechanism to switch direction. In one embodiment the dwell period is not discernable to the operator. Of course, other distances and speeds are contemplated and may be greater than zero mm and less than 1.5 mm and 1 mm respectively or equal to or greater than 1.5 mm and 1 mm respectively. Similarly, the speed may be greater than zero but less than 12 mm/sec or may be equal to or greater than 12 mm/sec. A jackhammer movement technique has been described in U.S. Pat. No. 9,220,568 incorporated herein by reference. In one embodiment the reverse movement is greater than the forward movement.

Figure 14:
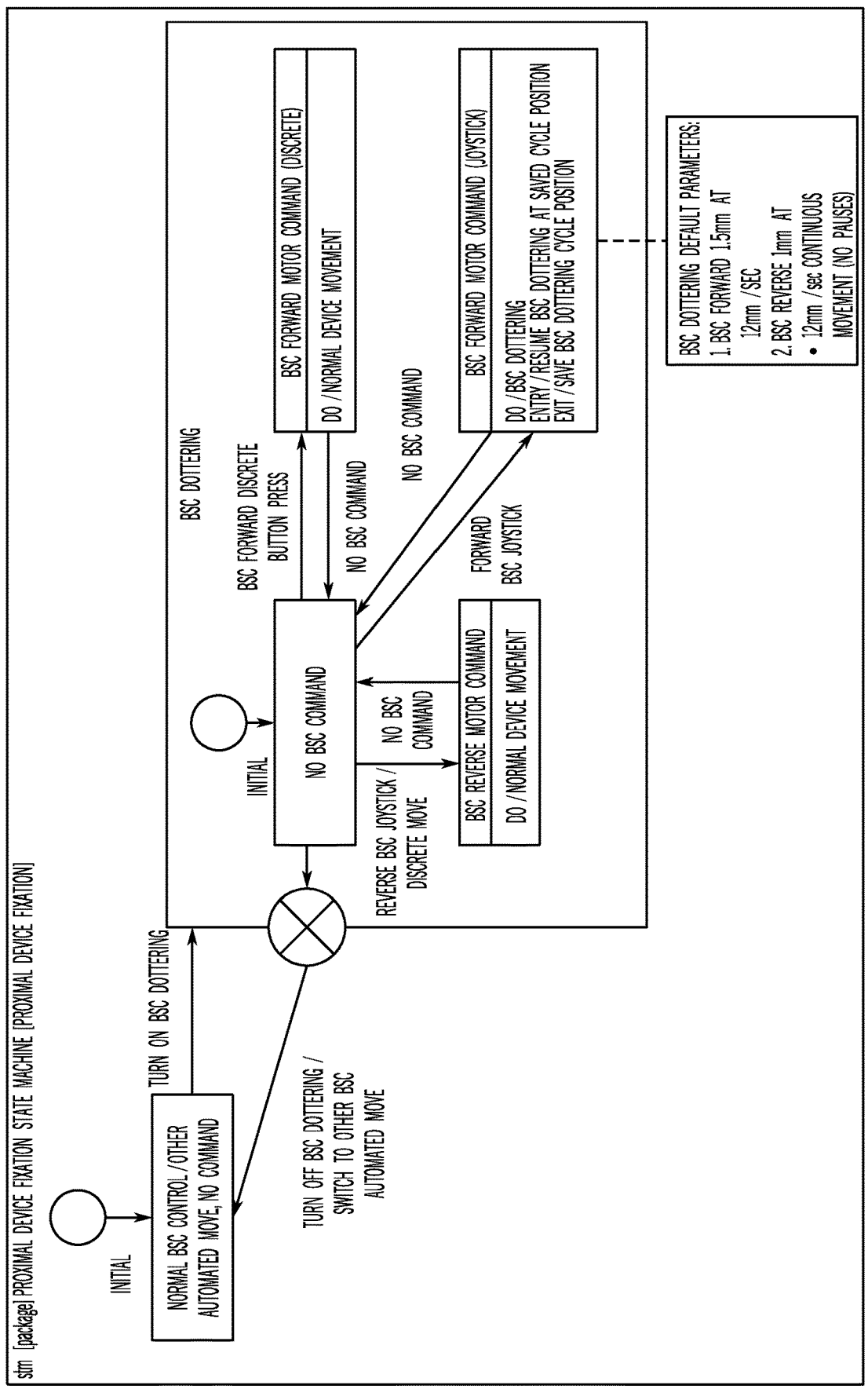

Referring now to FIG. 14, a state machine diagram is illustrated corresponding to another example of the jackhammer mode described above with reference to FIG. 6. In the example of FIG. 14, the jackhammer mode is applied to a balloon or stent catheter, also referred to herein as dottering. When the example mode of FIG. 14 is selected, there are a number of states that effect the movement of the balloon catheter or stent catheter (referred to herein individually and collectively as "BSC"). BSC can also include other elongated medical devices. The mode illustrated in FIG. 14 is similar to the mode of FIG. 13, but since there is no rotational drive of the BSC, the rotational aspect is not relevant.

Figure 15:
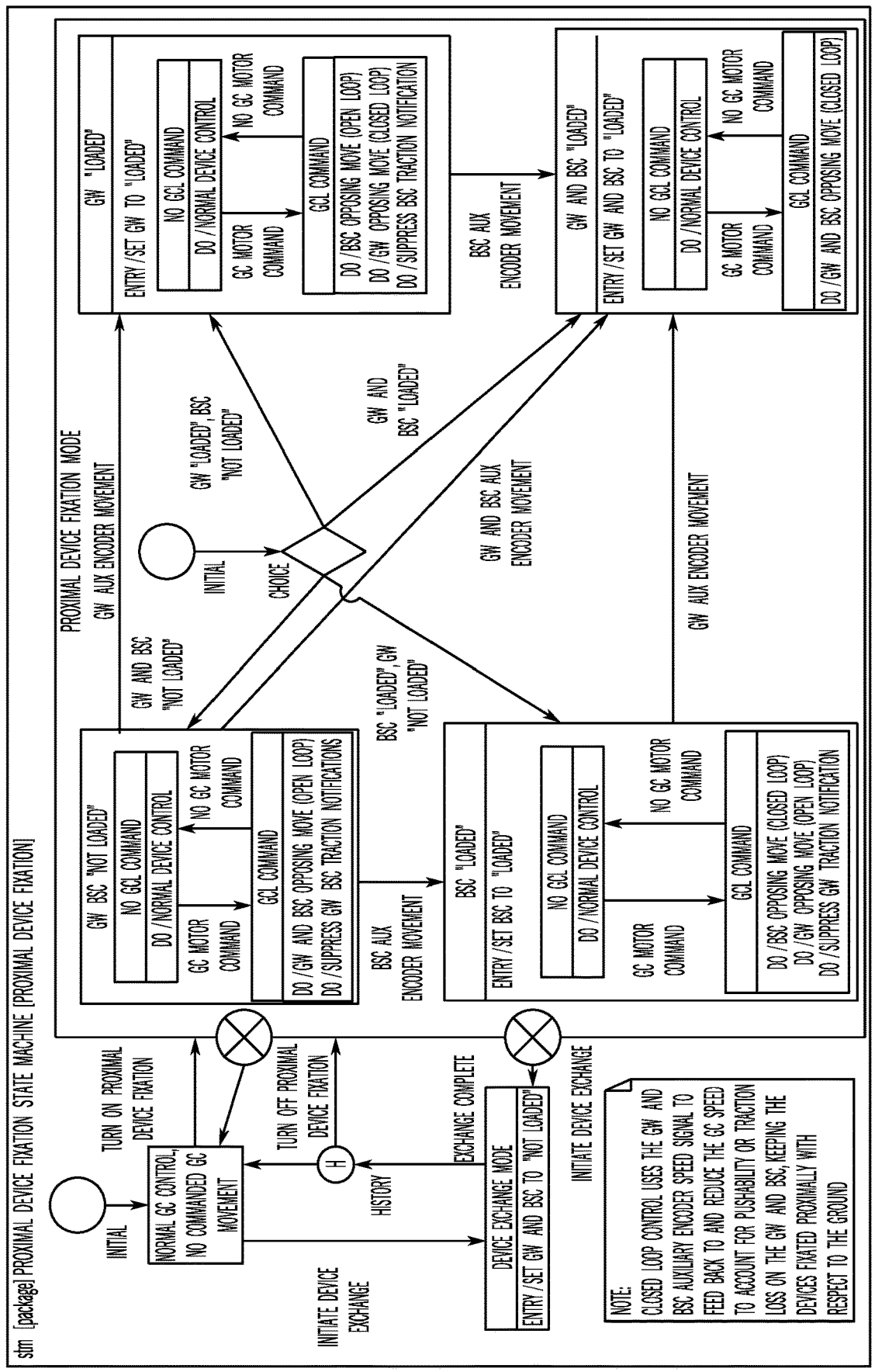
FIG. 15 is a state machine command diagram associated with example mode of FIGS. 7 and 8.
Figure 16A:
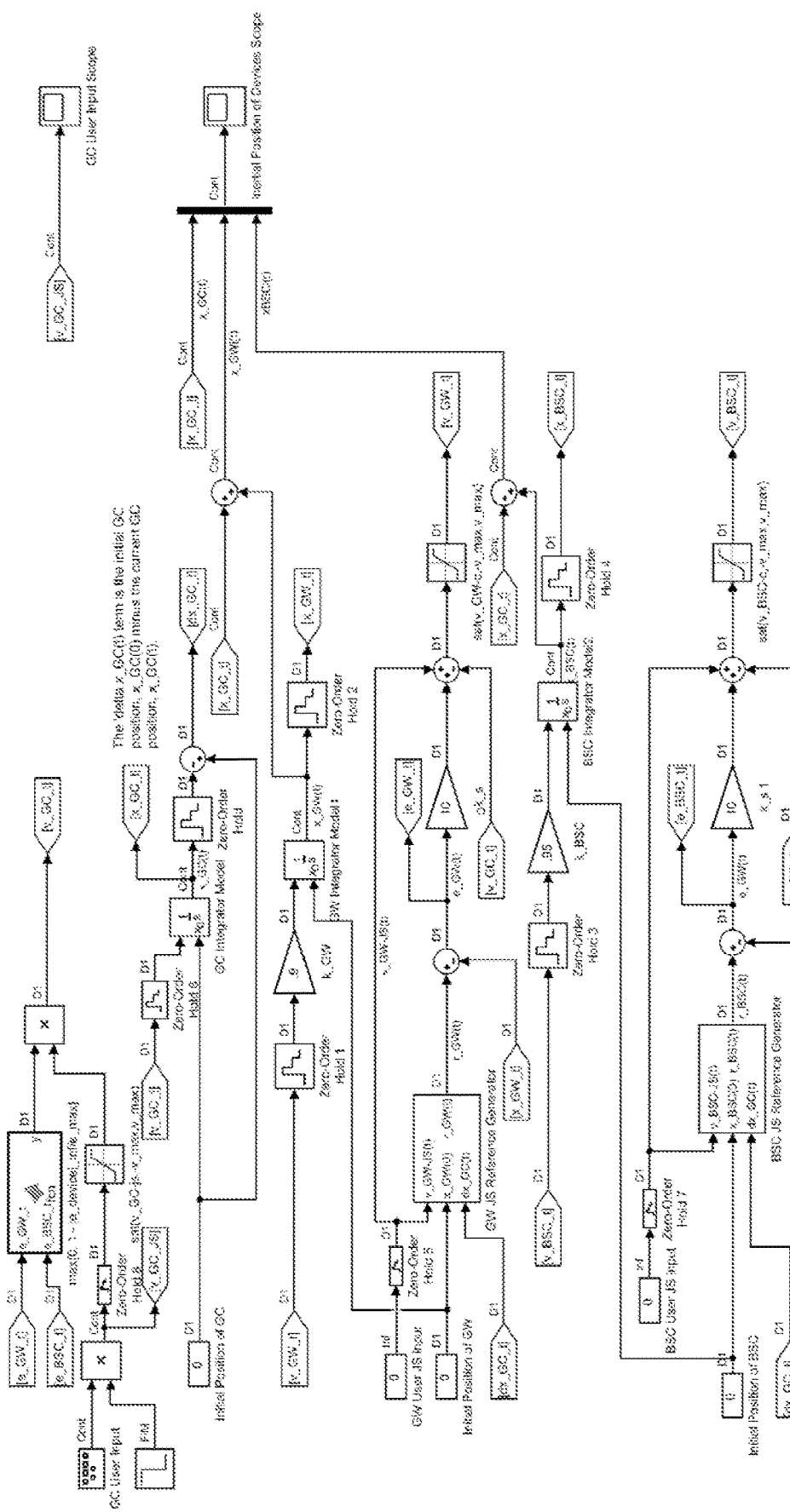
FIGS. 16A-D illustrate an example algorithm diagram for active device fixation.
Figure 16B:
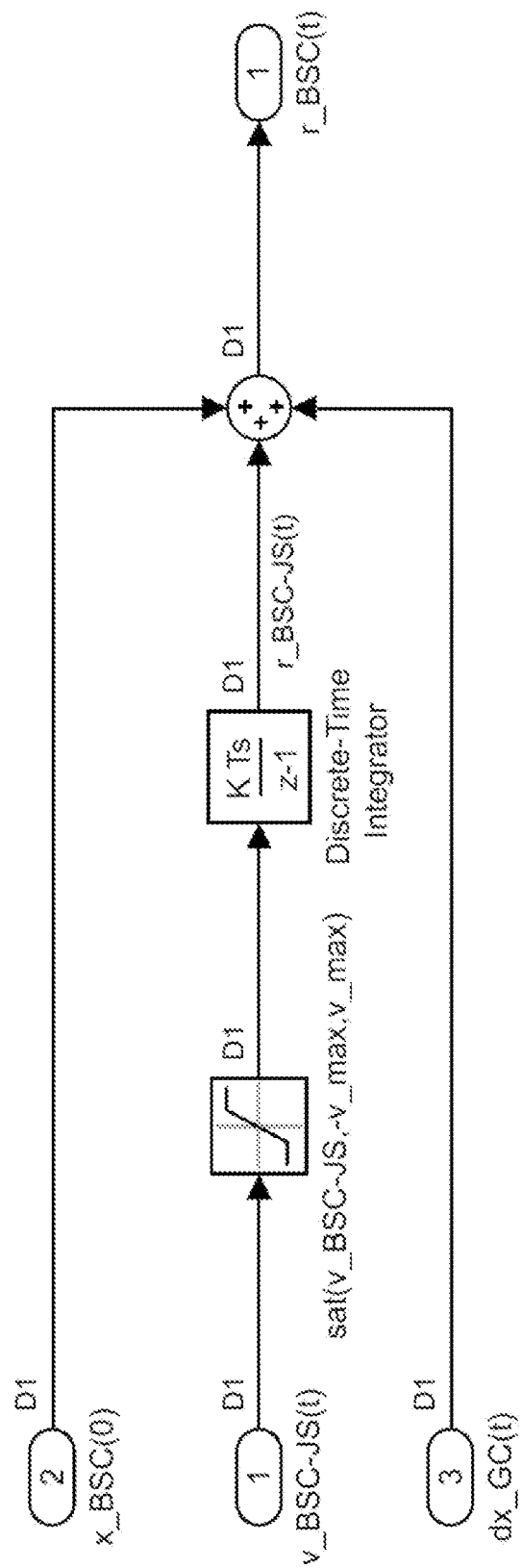
Figures 16C, 16D:
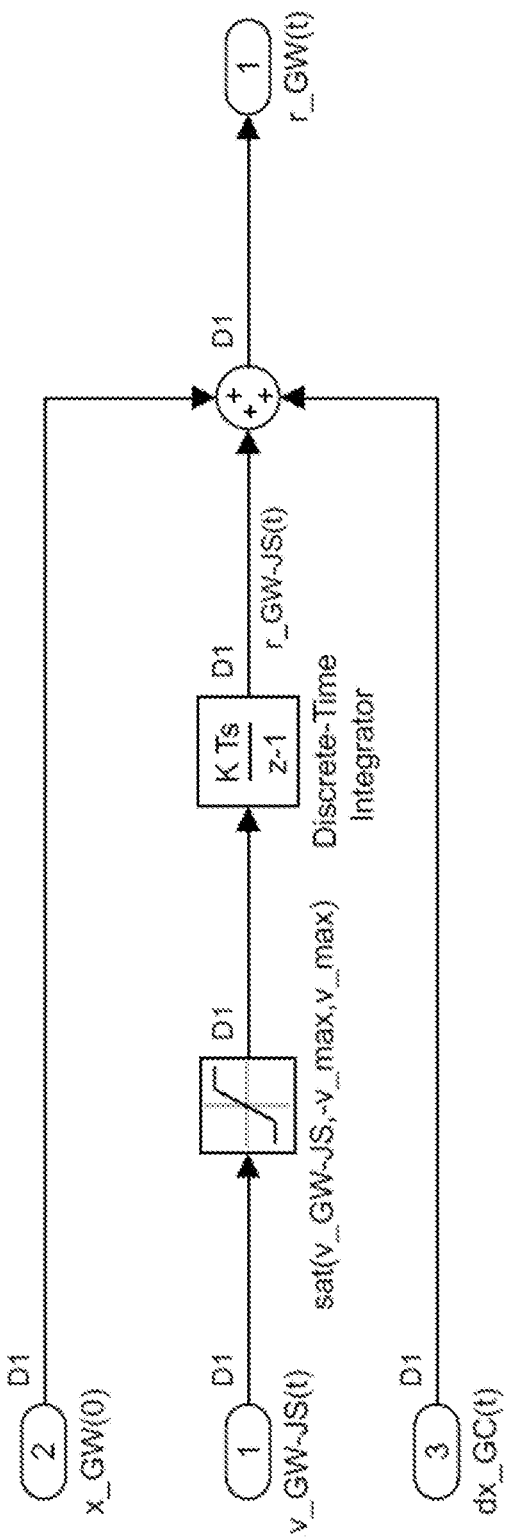

Referring to FIG. 15, a state machine diagram is illustrated corresponding to an example of the ADF mode described above with reference to FIGS. 7 and 8. In one example of the ADF mode, coordinated control is provided of one or two linear drive mechanisms that are on a similar base and move linearly together with the GC when the base is moved in a linear direction. The ADF mode allows the linear drive mechanisms of the guidewire and/or BSC to maintain a fixed position of the GW ad BSC relative to the earth or patient while moving the GC relative to the earth or patient. In one embodiment once the ADF movement algorithm has been selected and enabled the system detects if the guidewire and catheter are loaded or not loaded by automatically moving the guidewire and catheter a distance forward and reverse and checks via position sensors whether the guidewire and catheter are loaded into the respective linear drive mechanisms. In one embodiment this forward and reverse movement is referred to as a perturbation and moves the guidewire forward 0.1 mm and then reverse the same distance. However other distances greater or less than 0.1 mm such as 1 mm or 0.01 mm are contemplated. The distance is selected to both be detected by sensors as well as to minimize impact to procedure risk profile. In one embodiment the device detection system may be a positive device detector such as an optical sensor, mechanical sensor and magnetic sensor. In a first GW and BSC not loaded state in which no GC linear command has been given that is in which no instruction has been given by an operator via a user input to move the guide catheter fore or aft along the longitudinal axis of the guide catheter the GW and BSC linear drive mechanisms move the GW and BSC respectively in an equal and opposite direction than the guide catheter is moved. By way of example if the guide catheter is moved 1 cm in a forward direction, the drive mechanisms for the guidewire and BSC move the guidewire and BSC 1 cm in the reverse direction. This is done even if no GW and BSC is detected within the respective linear drive mechanisms. This device detection functionality allows for the successful use of ADF when only one of two or more possible fixated devices are loaded. If closed loop control was always enabled for all fixated device drive modules, when a device was not loaded, the system would prevent all movement of all devices due to the inability to fixate the not-loaded device. Additionally, the device detection functionality also provides a failsafe mechanism if sensors fail to detect the presence of the guidewire and BSC. In one embodiment in this mode the GW and BSC traction notifications are suppressed. The traction notification provides an alert if the sensors do not detect the GW and BSC moving at the rate intended by the controller.

Once a user provides input to linearly move the guide catheter either through a primary user input or a specific guide catheter user input by moving the entire base, and therefore the linear drive mechanism for the guidewire and linear drive mechanism for the BSC, a command is automatically given to the linear drive mechanism for the guidewire and the linear drive mechanism for the BSC to linearly move the guidewire and the catheter an equal distance in an opposite direction that the guide catheter is being moved. In one embodiment the movement of the guide catheter in a first direction is simultaneous with the movement of the guidewire and BSC in a direction opposite to the first direction. In one embodiment, the command to provide opposite movement to the guidewire and BSC when the user input providing movement instruction for the guide catheter only occurs once the guide catheter user input is beyond a dead band.

In a GW loaded state in which the guidewire is detected as loaded and the BSC is detected as not loaded, neither the guidewire nor the BSC is moved if there is no command to move the guide catheter linearly. However when a GC user input is moved or activated to move the guide catheter linearly, a command is automatically provided to the guidewire linear drive mechanism to move in the opposite direction an amount equal to maintain the position of the guidewire in a fixed location even if the required amount of movement by the guidewire linear drive mechanism to maintain this position is different than the amount of movement provided to the guide catheter linear drive mechanism. In this manner a closed loop control is provided. In contrast, in this command state the linear drive mechanism of the BSC moves an amount equal and opposite to the movement provided by the guide catheter linear drive.

In the GW and BSC loaded state both the guidewire linear drive mechanism and the BSC linear drive mechanism move the guidewire and BSC respectively in the opposite direction of the movement of the guide catheter, but the amount of movement is set such that the GW and BSC remain in a fixed position relative to the patient and/or earth. In this manner a closed loop control is provided for both GW and BSC.

In one embodiment in the closed loop system of moving the GW and BSC a sensor such as an encoder coupled to a tire is used to determine if the GW and BSC positions are such that they have moved appropriately equal and opposite to the movement of the GC. If the encoders provide feedback that the GW and/or BSC are at a position that is less than appropriately equal and opposite to the position change of the GC, then a command is automatically sent to the GC linear drive mechanism to slow down movement of the GC until the GW and BSC return to an appropriately equal and opposite relative position. By way of example if a guide catheter user input instructs the guide catheter to move forward 10 units and the encoders indicate that that the GW has moved in an opposite direction but only a distance of 8 units, then the GC linear drive mechanism will be automatically be slowed until the GW and/or BSC are in sync having moved the equal and opposite distance of the GC. Once the GW and/or BSC are in a synced state the GC linear drive will accelerate back to its originally intended movement speed. In one embodiment when slippage is detected in the GW and/or BSC the GW and/or BSC drive mechanisms increase the velocity of the GW and BSC linear movement until the GW and/or BSC are in a synced state with the GC. In one embodiment the GC is slowed down and the GW and/or BSC as needed are simultaneously accelerated. The synced state is one in which the GW and BSC remain in a fixed location relative to the earth and/or patient during movement of the GC.

In one embodiment the movement of the GW and/or BSC is not a fixed equal and opposite amount but at a velocity different that the velocity of the GC.

In one embodiment, auxiliary encoders are used to provide a closed loop control system for fixing the GW and/or BSC devices during the ADF movement technique.

In one embodiment the ADF movement technique stops movement of the GC if spatial fixation of the GW and/or BSC is not possible according to control law.

In one embodiment auxiliary encoders detect if devices are loaded into the GW linear drive and/or BSC linear drive by detecting movement of the auxiliary encoders. If no movement is detected, it is assumed that no device is loaded. In this embodiment no determination is made as to whether there are devices loaded into the linear drive mechanisms but rather only checked upon a first command for movement of the device or devices. If no device is detected as loaded, an open loop control is used for fixation to protect against single fault of auxiliary encoder failure.

In one embodiment a user may provide for manual adjustment during the ADF movement technique by manually manipulating the user inputs for the GW and/or BSC. The instruction to move the GW and/or BSC linearly by the user will supplement the automatic movement. In one embodiment the operator instruction to move the GW and BSC linearly during the ADF movement technique will temporarily suspend the ADF movement technique until the user ceases to provide independent GW or BSC linear movement instructions.

Referring to FIGS. 16A-16D, in one embodiment an Active Device Fixation (ADF) movement consists of fixing a device position relative to the earth or the patient, the devices inertial position. It is assumed that the inertial position of each device translates in the same direction that the GC translates. Therefore, in order to maintain the position of a device its position should move opposite the direction of the GC once ADF is enabled. The position of the GC xGC(t) (denoted x_GC_t) is the integral of the command velocity, vGC(t) (denoted v_GC_t). This relationship is captured by the GC Integrator Model.

$$x_{GC}(t) = \int v_{GC}(t)dt$$

The position of the GW xGW(t) (denoted x_GW_t) is the integral of the scaled GW command velocity vGW(t) (denoted v_GW_t) which is scaled by the real number kGW (denoted k_GW).

$$x_{GW}(t) = \int k_{GW} v_{GW}(t)dt$$

As such GW slipping can be captured in this physical model in which $0 < k_{GW} < 1$. Complete GW slipping would occur if $k_{GW}$ is zero. The resulting inertial position of the GW, $X_{GWi}$ (which we denote x_GWi(t)), is the sum of $x_{GW}(t)$ and the GC position xGC(t). Similarly, the physical model for the BSC is as follows $$x_{BSC}(t) = \int k_{BSC} v_{BSC}(t)dt$$

In which the command velocity to the BSC, $v_{BsG}$, is denoted as as v_BSC(t) and its corresponding position, $X_{BSC}$, is denoted as x_BSC(t). The resulting inertial position of the BSC, $X_{BSCi}$ (which we denote x_BSCi(t)), is the sum of $x_{BSC}(t)$ and the GC position xGC(t).

In one embodiment of the ADF movement technique acts to fix the inertial position of the GW and BSC; allow the user to move the GW and BSC independent of GC motion with a joystick (JS) command; and reduce the forward (FWD) and reverse (REV) motion of the GC when slipping of the GW is excessive and corrective motions need to catch up.

In one embodiment the inertial position of the GW and BSC by feeding in the negative command velocity of the GC to the GW and BSC respectively along; and adjusting the velocity of the GW and BSC proportional to their corresponding feedback terms, (e_BSC_t, e_GW_t) which include the negative change in position of the GC (dx_GC_t). Where e_BSC_t equals (r_BSC_t−x_BSC_t) where r_BSC_t is the integral of the sum of the limited BSC Joystick velocity and the ADF feedback term dx_GC(t). In which dx_GC(t) equals the initial GC position, x_GC(0) minus the current GC position, x_GC(t).

*** Where e_GW_t equals (r_GW_t−x_GW_t) where r_GW_t is the integral of the sum of the limited GW Joystick velocity and the ADF feedback term dx_GC(t).

In one embodiment of the ADF technique the user is permitted to move the GW and BSC independent of GC motion by including a reference term which is the integral of their respective velocity commands. The FWD and REV motion of the GC is reduced as the feedback errors grow due to slipping of the GW and BSC devices (function y=fcn (e_GW_t, e_BSC_t)).

Referring to FIG. 16 that the terms of 0.9 and 0.95 of the GW and BSC controls represent the slippage of the GW and BSC in one simulation. Or stated another way the 0.9 represents that the GW is 10 percent slipping and the 0.95 represents that the BSC is 5 percent slipping. The 0.9 and 0.95 are provided in the control system from an encoder detecting slippage of the GW ad BSC respectively. The actual percent of slippage of the GW and BSC are determined using encoders or other sensors during operation of the ADF technique.

Active device fixation may be accomplished in another embodiment in which the GW and the BSC are fixated relative to the earth and/or patient using a mechanical clamping device. The clamping device selectively fixates the devices during GC movement. In one embodiment the GW and BSC are fixated relative to earth with a dynamic device such as a robotic arm that act to maintain the relative position while the GC is being moved. In one embodiment GC movement is automatically stopped if the GW or BSC movement is detected such as by a sensor/or imaging system.

Referring to FIG. 16 the system denoted max{0, 1−|e_device|_inf/e_max} limits the command velocity to the GC when the feedback error for the GW or BSC as follows:

$$v_{GC}(t) = v_{GC\text{-}SET}(t) \times \max\left\{0, 1 - \frac{|e_{device}|}{e_{max}}\right\}$$

where $e_{device}$ is either the maximum of the error of the GW or BSC. Such that the final GC velocity is reduced in order to ensure the GC motion is bounded due to device slippage. Where $v_{GC\text{-}SET}(t)$ denotes the user GC joystick (user input) velocity set point. Where $e_{max}$ is the maximum allowable tracking error between the GC and the GW or BSC positions.

Computer-executable instructions for the steps of example methods 300 and 400 may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

Figure 17:
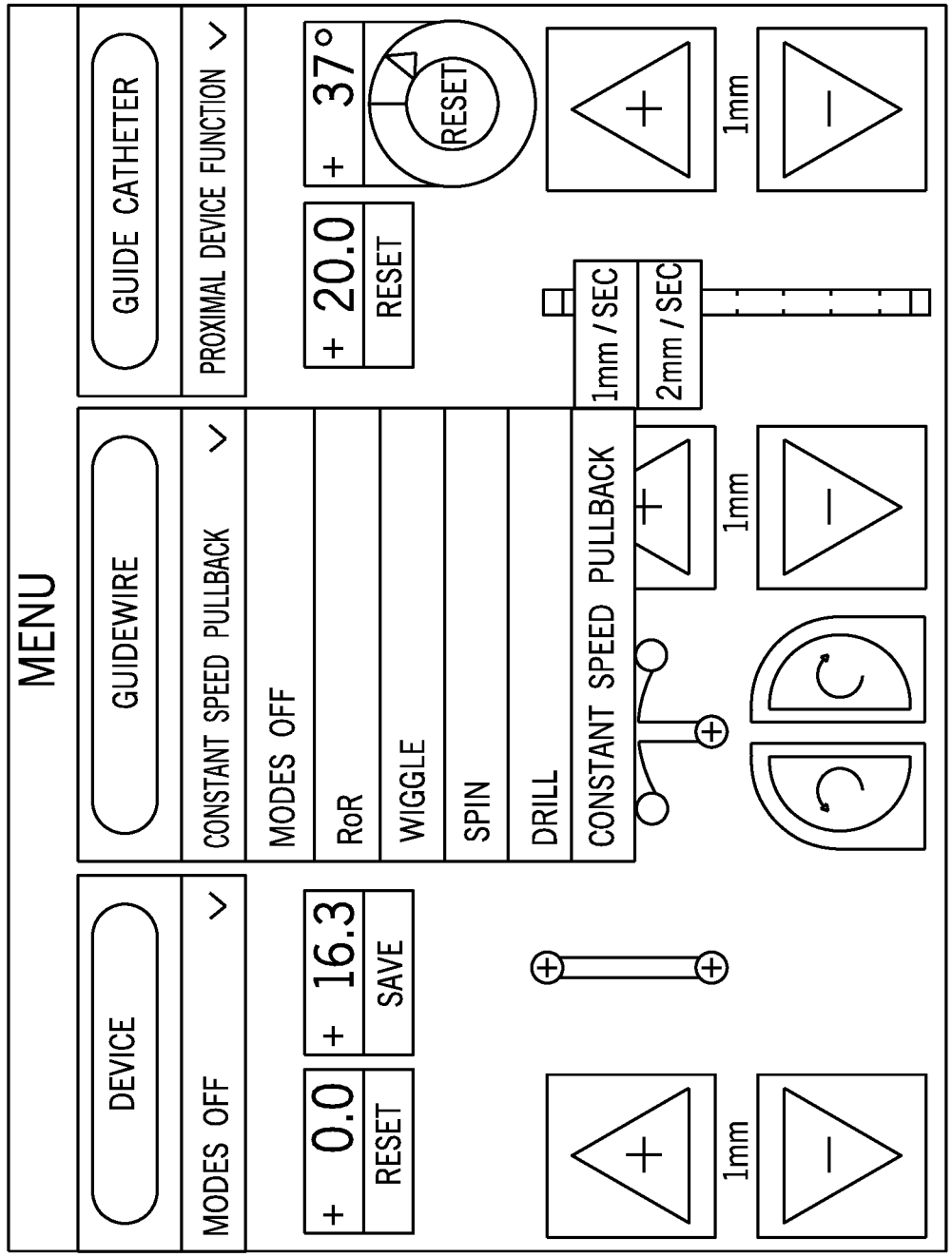
FIG. 17 illustrates an example graphical user interface.

Referring to FIG. 17 a Constant Speed Pullback movement technique was selected for the GW. In one embodiment the speed of the constant speed may be selected from a number of choices or a specific speed may be input via a user device such as a keyboard. In this any movement by the operator of the primary user interface in a reverse direction will withdraw the GW at a constant speed. In one embodiment the constant speed movement technique only effects the reverse direction, that is, the reverse direction is a constant speed regardless of the extent of movement position of the primary user interface in the reverse direction. Movement of the primary user interface in the forward direction will be proportional or otherwise based on extent of movement of the primary interface.

In one embodiment constant speed movement technique also allows for constant speed of the GW in a forward direction. In one embodiment a turbo input button allows the constant speed to increase to a faster speed. In one embodiment the increase constant speed will be only while a user is holding the turbo button. In one embodiment the increase in constant speed will remain in effect once the turbo button is pushed and will remain in effect until the turbo button is switched off. In one embodiment the increased constant speed will remain in effect for a predetermined amount of time and/or a predetermined distance of linear travel of the GW.

Although not illustrated, a Pushability Override input allows increased push force only if initial push force limit is hit during device forward movement. In this mode the motor current increases torque for forward motion before it stalls (over the predetermined limit). In one embodiment the force increases for the entire procedure or allow an increase in force for a limited period of time after the initial force limit is hit. In one embodiment a user may revert to a lower predetermined or selected force limit by unselecting the pushability override feature.

In one embodiment, a technique (ADF, wiggle, jackhammer) can be independently selected for each EMD in the catheter-based procedure system. For example, ADF could be selected for the guide catheter, wiggle could be selected for the guidewire, and dottering could be selected for the BSC.

In one embodiment multiple techniques may be used simultaneously. In one embodiment once a particular technique has been selected all other incompatible techniques are no longer available for selection. In one embodiment the available techniques available for selection may be based on image and/or other patient data such as but not limited to hemodynamic data. In one embodiment particular techniques may be automatically highlighted and recommended for selection based on processing of image data.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:
1. A system, comprising:
an apparatus configured to cause movement of a first elongated medical device and of a second elongated medical device; and
a controller coupled to the apparatus, the controller configured to:
determine a magnitude and a direction of linear translation of the first elongated medical device, and
responsive to the determined linear translation of the first elongated medical device, control the apparatus to cause a linear translation of the second elongated medical device, the linear translation of the second elongated device having a substantially equal magnitude to the linear translation of the first elongated medical device and being in a direction opposite the direction of the linear translation of the first elongated medical device,
wherein the controller is further configured to modify at least one parameter of the linear translation of either (a) the first elongated medical device or (b) the second elongated medical device.
2. The system of claim 1, wherein modifying the at least one parameter includes:
limiting the magnitude of the linear translation of the second elongated medical device.
3. The system of claim 2, wherein the controller modifies the at least one parameter in response to a determination of a loss of traction for the linear translation of the second elongated medical device.
4. The system of claim 1, wherein the at least one parameter includes:

the magnitude or speed of the linear translation of the first elongated medical device.

5. The system of claim 1, wherein the first elongated medical device is a catheter and the second elongated medical device is a guidewire.

6. The system of claim 1, wherein the linear translation of the first elongated medical device and the linear translation of the second elongated medical device are substantially simultaneous.

7. The system of claim 1, wherein the controller identifies an unintended movement of the second elongated medical device, and wherein the controller suspends modification of the at least one parameter of the first elongated medical device or the second elongated medical device upon the identification of the unintended movement of the second elongated medical device.

8. The system of claim 1, wherein the controller detects an absence or a presence of the second elongated medical device based on detection of movement of the second elongated medical device via an input from a sensor.

9. The system of claim 8, wherein the controller suspends modification of the at least one parameter of the first elongated medical device or the second elongated medical device when the controller detects the absence of the second elongated medical device.

10. The system of claim 1, wherein the controller terminates the linear translation of the second elongated medical device when the linear translation of the second elongated medical device is within a first threshold of the determined translation of the first elongated medical device.

11. The system of claim 10, wherein the controller resumes the linear translation of the second elongated medical device when the linear translation of the second elongated medical device is greater than a second threshold of the determined linear translation of the first elongated medical device, wherein the second threshold is greater than the first threshold.

12. A system, comprising:
an apparatus configured to cause movement of a first elongated medical device and of a second elongated medical device; and
a controller coupled to the apparatus, the controller configured to:
receive a command to move the first elongated medical device;
control the apparatus to move the first elongated medical device in response to the command;
detect the movement of the first elongated medical device; and
responsive to the detected movement of the first elongated medical device, control the apparatus to synchronize movement of the second elongated medical device to the movement of the first elongated medical device.

13. The system of claim 12, wherein the movement of the first elongated medical device and the synchronized movement of the second elongated medical device includes small alternatingly forward and backward linear movements with a resultant forward linear translation.

14. A method comprising:
determining a magnitude and a direction of linear translation of a first elongated medical device,
responsive to determining the magnitude and the direction of the linear translation of the first elongated medical device, causing a linear translation of a second elongated medical device, the linear translation of the second elongated medical device having a substantially equal magnitude to the linear translation of the first elongated medical device and being in a direction opposite the direction of the linear translation of the first elongated medical device; and
modifying at least one parameter of the linear translation of either (a) the first elongated medical device or (b) the second elongated medical device.

15. The method of claim 14, wherein modifying the at least one parameter includes:
limiting the magnitude of the linear translation of the second elongated medical device.

16. The method of claim 15, wherein the at least one parameter is modified in response to determining a loss of traction for the linear translation of the second elongated medical device.

17. The method of claim 14, wherein the at least one parameter includes:
the magnitude or speed of the linear translation of the first elongated medical device.

18. The method of claim 14, further comprising:
identifying an unintended movement of the second elongated medical device; and
in response to identifying the unintended movement of the second elongated medical device, suspending modification of the at least one parameter of the first elongated medical device or the second elongated medical device.

19. The method of claim 14, further comprising:
determining the linear translation of the second elongated medical device is within a first threshold of the determined translation of the first elongated medical device; and
in response to determining the linear translation of the second elongated medical device is within the first threshold of the determined translation of the first elongated medical device, terminating the linear translation of the second elongated medical device.

* * * * *